US012430484B2

(12) United States Patent
Niroula et al.

(10) Patent No.: US 12,430,484 B2
(45) Date of Patent: Sep. 30, 2025

(54) ACCELERATED MOLECULAR DYNAMICS SIMULATION METHOD ON A COMPUTING SYSTEM

(71) Applicants: IONQ, INC., College Park, MD (US); University of Maryland, College Park, MD (US)

(72) Inventors: Pradeep Niroula, College Park, MD (US); Wengang Zhang, Gaithersburg, MD (US); Yunseong Nam, North Bethesda, MD (US)

(73) Assignees: UNIVERSITY OF MARYLAND, COLLEGE PARK, College Park, MD (US); IONQ, INC., College Park, MD (US)

( * ) Notice: Subject to any disclaimer, the term of this patent is extended or adjusted under 35 U.S.C. 154(b) by 986 days.

(21) Appl. No.: 17/531,366

(22) Filed: Nov. 19, 2021

(65) Prior Publication Data

US 2022/0198105 A1    Jun. 23, 2022

Related U.S. Application Data

(60) Provisional application No. 63/133,111, filed on Dec. 31, 2020, provisional application No. 63/129,449, filed on Dec. 22, 2020.

(51) Int. Cl.
G06F 30/25 (2020.01)
G06N 10/80 (2022.01)

(52) U.S. Cl.
CPC ............ *G06F 30/25* (2020.01); *G06N 10/80* (2022.01)

(58) Field of Classification Search
CPC ......... G06F 30/25; G06F 30/20; G06N 10/80; G06N 10/60; G06N 10/40; G16C 20/30; G16C 10/00
See application file for complete search history.

(56) References Cited

PUBLICATIONS

Shokri et al. Implementation of a Quantum Algorithm to Estimate the Energy of a Particle in a Finite Square Well Potential on IBM Quantum Computer Islamic Azad Univeristy, Tehran, Aug. 18, 2021 (Year: 2021).*

(Continued)

*Primary Examiner* — Jay Hann
*Assistant Examiner* — Cuong V Luu
(74) *Attorney, Agent, or Firm* — Patterson + Sheridan, LLP

(57) ABSTRACT

A method of performing a computational process includes transforming, a first register of a quantum processor to a charge encoded state in which charges of interacting particles to be simulated are encoded, transforming a second register of the quantum processor to a position encoded state in which positions of the interacting particles are encoded, performing a first phase shift operation, including shifting a phase of the first and second registers by kinetic energies of the interacting particles, performing a second phase shift operation, including shifting the phase of the first and second registers by pair-wise Coulomb potential energies of the interacting particles, measuring the phase of the first and second registers, transmitting the measured phase of the first and second registers to a classical computer, and the measured phase including a sum of the kinetic energies and the pair-wise Coulomb potential energies of the interacting particles.

20 Claims, 6 Drawing Sheets

(56) References Cited

PUBLICATIONS

Schindler et al. A Quantum Information Processor With Trapped Ions Aug. 14, 2013 (Year: 2013).*
Magann et al. Digital Quantum Simulation of Molecular Dynamics and Control PHysical Review Research 3, 023165, Jun. 2021 (Year: 2021).*
R. Babbush, D. W. Berry, J. R. McClean, and H. Neven, Quantum simulation of chemistrywith sublinear scaling in basis size, npj Quantum Information, 5 (2019).
M. Bonitz, P. Ludwig, H. Baumgartner, C. Henning, A. Filinov, D. Block, O. Arp, A. Piel, S. Kading, Y. Ivanov, et al., Classical and quantum coulomb crystals, Physics of Plasmas, 15 (2008), p. 4717.
D. Frenkel and B. Smit, Understanding molecular simulation: from algorithms to applications, vol. 1, Elsevier, 2001.
I. Kassal, S. P. Jordan, P. J. Love, M. Mohseni, and A. Aspuru-Guzik, Polynomial-time quantum algorithm for the simulation of chemical dynamics, Proceedings of the National Academy of Sciences, 105 (2008), pp. 18681-18686.
I. D. Kivlichan, C. Gidney, D. W. Berry, N. Wiebe, J. McClean, W. Sun, Z. Jiang, N. Rubin, A. Fowler, A. Aspuru-Guzik, et al., Improved fault-tolerant quantum simulation of condensed-phase correlated electrons via trotterization, Quantum, 4 (2020), p. 296.
I. D. Kivlichan, N. Wiebe, R. Babbush, and A. Aspuru-Guzik, Bounding the costs of quantum simulation of many-body physics in real space, Journal of Physics A: Mathematical and Theoretical, 50 (2017), p. 305301.

* cited by examiner

700

```
┌─────────────────────────────────────────────────────────────┐
│ TRANSFORM, BY A SYSTEM CONTROLLER, A FIRST REGISTER OF A    │ ─ 710
│ QUANTUM PROCESSOR TO A CHARGE ENCODED STATE IN WHICH        │
│ CHARGES OF A PLURALITY OF INTERACTING PARTICLES TO BE       │
│ SIMULATED ARE ENCODED                                       │
└─────────────────────────────────────────────────────────────┘
```

- 710
- 720
- 730
- 740
- 750
- 760
- 770

TRANSFORM, BY A SYSTEM CONTROLLER, A FIRST REGISTER OF A QUANTUM PROCESSOR TO A CHARGE ENCODED STATE IN WHICH CHARGES OF A PLURALITY OF INTERACTING PARTICLES TO BE SIMULATED ARE ENCODED

TRANSFORM, BY THE SYSTEM CONTROLLER, A SECOND REGISTER OF THE QUANTUM PROCESSOR TO A POSITION ENCODED STATE IN WHICH POSITIONS OF THE PLURALITY OF INTERACTING PARTICLES ARE ENCODED

PERFORM A FIRST PHASE SHIFT OPERATION, COMPRISING SHIFTING, BY THE SYSTEM CONTROLLER, A PHASE OF THE FIRST AND SECOND REGISTERS BY KINETIC ENERGIES OF THE PLURALITY OF INTERACTING PARTICLES

PERFORM A SECOND PHASE SHIFT OPERATION, COMPRISING SHIFTING, BY THE SYSTEM CONTROLLER, THE PHASE OF THE FIRST AND SECOND REGISTERS BY PAIR-WISE COULOMB POTENTIAL ENERGIES OF THE PLURALITY OF INTERACTING PARTICLES

MEASURE, BY THE SYSTEM CONTROLLER, THE PHASE OF THE FIRST AND SECOND REGISTERS

TRANSMIT, BY THE SYSTEM CONTROLLER, THE MEASURED PHASE OF THE FIRST AND SECOND REGISTERS TO A CLASSICAL COMPUTER, THE MEASURED PHASE COMPRISING A SUM OF THE KINETIC ENERGIES AND THE PAIR-WISE COULOMB POTENTIAL ENERGIES OF THE PLURALITY OF INTERACTING PARTICLES

OUTPUT, BY THE CLASSICAL COMPUTER, RESULTS OF SIMULATION OF THE PLURALITY OF INTERACTING PARTICLES THAT ARE BASED ON THE MEASURED PHASE TRANSMITTED FROM THE SYSTEM CONTROLLER, WHEREIN THE RESULTS OF THE SIMULATION ARE CONFIGURED TO BE DISPLAYED ON A USER INTERFACE, STORED IN A MEMORY OF THE CLASSICAL COMPUTER, OR TRANSFERRED TO ANOTHER COMPUTATIONAL DEVICE

*Fig. 7*

ACCELERATED MOLECULAR DYNAMICS SIMULATION METHOD ON A COMPUTING SYSTEM

CROSS-REFERENCE TO RELATED APPLICATIONS

This application claims the benefit of the U.S. Provisional Patent Application Ser. No. 63/129,449, filed on Dec. 22, 2020, and Ser. No. 63/133,111, filed on Dec. 31, 2020, each of which is incorporated by reference herein.

GOVERNMENT LICENSE RIGHTS

This invention was made with Government support under 70NANB16H168 awarded by the National Institute of Standards and Technology. The Government has certain rights in the invention.

BACKGROUND

Field

The present disclosure generally relates to a method of performing computation in a quantum computing system, and more specifically, to a method of obtaining energies of a system having interacting particles by molecular dynamics (MD) simulations in a quantum computing system that includes a group of trapped ions.

Description of the Related Art

Among physical systems upon which it is proposed to build large-scale quantum computers, is a group of ions (e.g., charged atoms), which are trapped and suspended in vacuum by electromagnetic fields. The ions have internal hyperfine states which are separated by frequencies in the several GHz range and can be used as the computational states of a qubit (referred to as "qubit states"). These hyperfine states can be controlled using radiation provided from a laser, or sometimes referred to herein as the interaction with laser beams. The ions can be cooled to near their motional ground states using such laser interactions. The ions can also be optically pumped to one of the two hyperfine states with high accuracy (preparation of qubits), manipulated between the two hyperfine states (single-qubit gate operations) by laser beams, and their internal hyperfine states detected by fluorescence upon application of a resonant laser beam (read-out of qubits). A pair of ions can be controllably entangled (two-qubit gate operations) by qubit-state dependent force using laser pulses that couple the ions to the collective motional modes of a group of trapped ions, which arise from their Coulombic interaction between the ions. In general, entanglement occurs when pairs or groups of ions (or particles) are generated, interact, or share spatial proximity in ways such that the quantum state of each ion cannot be described independently of the quantum state of the others, even when the ions are separated by a large distance.

Examples of applications in which such quantum computers can provide improvement over classical computers include simulations of a complex, physical, quantum system. In molecular dynamics (MD) simulations of a complex, physical, quantum system including a large number of interacting particles, the number of interaction terms to consider between particles, including long-range interactions, increases as $\mathcal{O}(\eta^2)$ as the number of interacting particle $\eta$ increases. Even with an efficient method, Ewald summation method, the number of interaction terms scales as $\mathcal{O}(\eta^{3/2})$.

Considering a simulation of a quantum system requires exponentially large classical computational resources, there is a need for method for using a quantum processor as efficiently as possible to speed up such simulations.

SUMMARY

Embodiments of the present disclosure provide a method of performing a computational process using a quantum computing system. The method includes transforming, by a system controller, a first register of a quantum processor to a charge encoded state in which charges of a plurality of interacting particles to be simulated are encoded, transforming, by the system controller, a second register of the quantum processor to a position encoded state in which positions of the plurality of interacting particles are encoded, performing a first phase shift operation, including shifting, by the system controller, a phase of the first and second registers by kinetic energies of the plurality of interacting particles, performing a second phase shift operation, including shifting, by the system controller, the phase of the first and second registers by pair-wise Coulomb potential energies of the plurality of interacting particles, measuring, by the system controller, the phase of the first and second registers, transmitting, by the system controller, the measured phase of the first and second registers to a classical computer, the measured phase including a sum of the kinetic energies and the pair-wise Coulomb potential energies of the plurality of interacting particles, and outputting, by the classical computer, results of simulation of the plurality of interacting particles that are based on the measured phase transmitted from the system controller, wherein the results of simulation are configured to be displayed on a user interface, stored in a memory of the classical computer, or transferred to another computational device.

Embodiments of the present disclosure also a quantum computing system. The quantum computing system includes a quantum processor including a group of trapped ions, each trapped ion of the group of trapped ions having two hyperfine states defining a qubit, a system controller configured to transform a first register of a quantum processor to a charge encoded state in which charges of a plurality of interacting particles to be simulated are encoded, transform a second register of the quantum processor to a position encoded state in which positions of the plurality of interacting particles are encoded, perform a first phase shift operation, including shifting a phase of the first and second registers by kinetic energies of the plurality of interacting particles, perform a second phase shift operation, including shifting the phase of the first and second registers by pair-wise Coulomb potential energies of the plurality of interacting particles, measure, by the system controller, the phase of the first and second registers, and transmit the measured phase of the first and second registers to a classical computer, the measured phase including a sum of the kinetic energies and the pair-wise Coulomb potential energies of the plurality of interacting particles, and a classical computer configured to output results of simulation of the plurality of interacting particles that are based on the measured phase transmitted from the system controller, wherein the results of simulation are configured to be displayed on a user interface, stored in a memory of the classical computer, or transferred to another computational device.

Embodiments of the present disclosure further provide a quantum computing system including non-volatile memory having a number of instructions stored therein. The number of instructions which, when executed by one or more processors, causes the quantum computing system to perform operations including transforming, by a system controller, a first register of a quantum processor to a charge encoded state in which charges of a plurality of interacting particles to be simulated are encoded, transforming, by the system controller, a second register of the quantum processor to a position encoded state in which positions of the plurality of interacting particles are encoded, performing a first phase shift operation, including shifting, by the system controller, a phase of the first and second registers by kinetic energies of the plurality of interacting particles, performing a second phase shift operation, including shifting, by the system controller, the phase of the first and second registers by pair-wise Coulomb potential energies of the plurality of interacting particles, measuring, by the system controller, the phase of the first and second registers, transmitting, by the system controller, the measured phase of the first and second registers to a classical computer, the measured phase including a sum of the kinetic energies and the pair-wise Coulomb potential energies of the plurality of interacting particles, and outputting, by the classical computer, results of simulation of the plurality of interacting particles that are based on the measured phase transmitted from the system controller, wherein the results of simulation are configured to be displayed on a user interface, stored in a memory of the classical computer, or transferred to another computational device.

BRIEF DESCRIPTION OF THE DRAWINGS

So that the manner in which the above-recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

FIG. 7 depicts a flowchart illustrating a method used to perform a computation using a quantum computer system.

Figure 1:
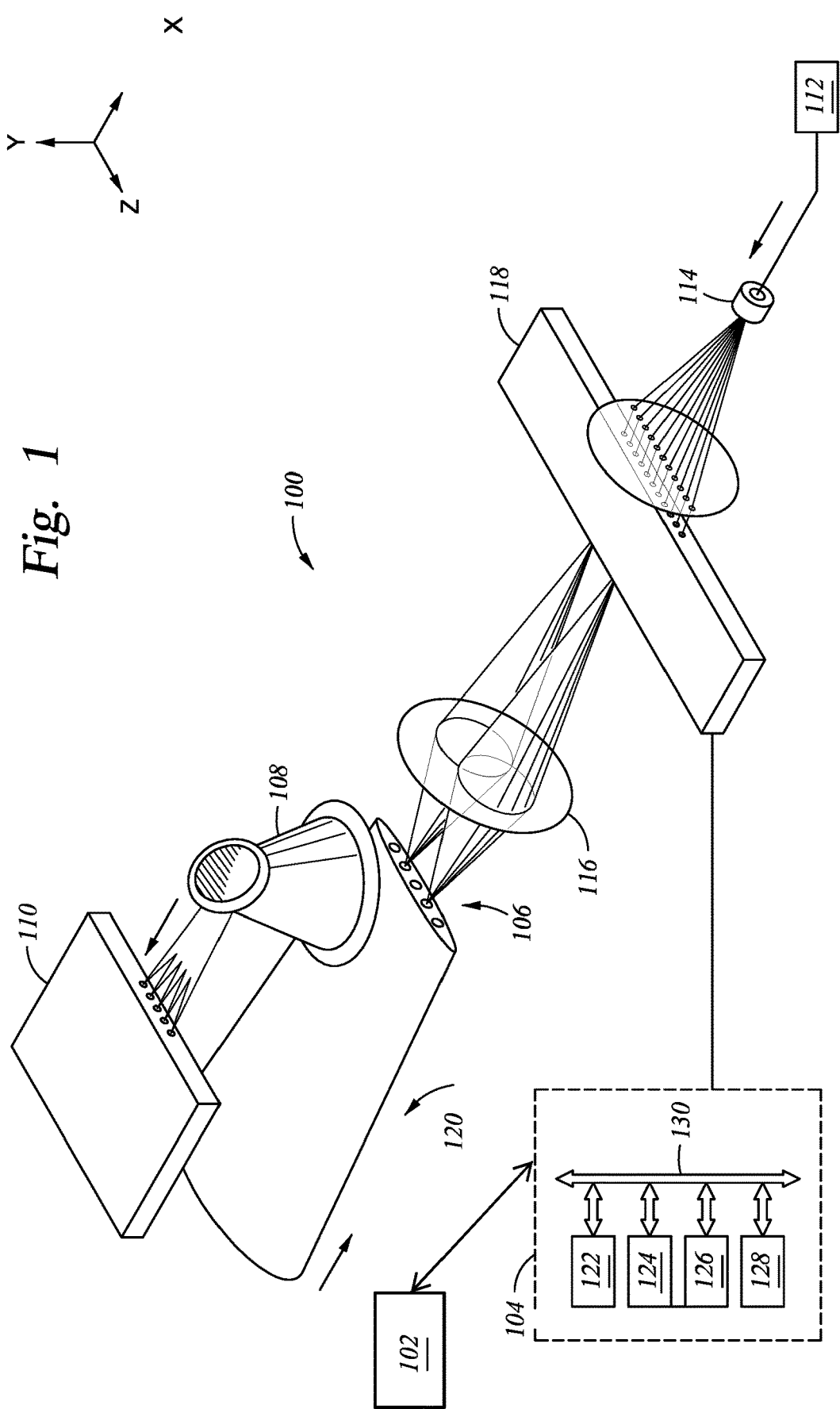
FIG. 1 is a schematic partial view of an ion trap quantum computing system according to one embodiment.

To facilitate understanding, identical reference numerals have been used, where possible, to designate identical elements that are common to the figures. In the figures and the following description, an orthogonal coordinate system including an X-axis, a Y-axis, and a Z-axis is used. The directions represented by the arrows in the drawing are assumed to be positive directions for convenience. It is contemplated that elements disclosed in some embodiments may be beneficially utilized on other implementations without specific recitation.

DETAILED DESCRIPTION

Embodiments described herein are generally related to methods of performing computation in a quantum computing system, and more specifically, to methods of computing energies of a system having interacting particles by molecular dynamics (MD) simulations in a quantum computing system that includes a group of trapped ions.

A quantum computing system that is able to compute energies of a system having interacting particles by molecular dynamics (MD) simulations may include a classical computer, a system controller, and a quantum processor. The classical computer performs supporting tasks including selecting a system of interacting particles to be simulated and outputting the computed energies of the system by use of a user interface. A software program for performing the tasks is stored in a non-volatile memory within the classical computer. The quantum processor includes trapped ions that are coupled with various hardware, including lasers to manipulate internal hyperfine states (qubit states) of the trapped ions and photomultiplier tubes (PMTs) to read-out the internal hyperfine states (qubit states) of the trapped ions. The system controller receives from the classical computer instructions for controlling the quantum processor, and controls various hardware associated with controlling any and all aspects used to run the instructions for controlling the quantum processor, and transmits a read-out of the quantum processor and thus output of results of the read-out to the classical computer. In some embodiments, the classical computer will then utilize the computational results based on the output of results of the read-out to form a results set that is then provided to a user the form of results displayed on a user interface, stored in a memory and/or transferred to another computational device for solving technical problems.

The methods and systems described herein include an efficient computer simulation routine executed by the quantum processor, within a quantum computing system, to perform computer simulation of a complex system. The methods described herein include improvements over conventional computer simulation methods.

I. General Hardware Configurations

FIG. 1 is a schematic partial view of an ion trap quantum computing system, or system 100, according to one embodiment. The system 100 includes a classical (digital) computer 102, a system controller 104 and a quantum processor that is a group 106 of trapped ions (i.e., five shown) that extend along the Z-axis. Each ion in the group 106 of trapped ions is an ion having a nuclear spin I and an electron spin S such that a difference between the nuclear spin I and the electron spin S is zero, such as a positive ytterbium ion, $^{171}Yb^+$, a positive barium ion $^{133}Ba^+$, a positive cadmium ion $^{111}Cd^+$ or $^{113}Cd^+$, which all have a nuclear spin I=½ and the $^2S_{1/2}$ hyperfine states. In some embodiments, all ions in the group 106 of trapped ions are the same species and isotope (e.g., $^{171}Yb^+$). In some other embodiments, the group 106 of trapped ions includes one or more species or isotopes (e.g., some ions are $^{171}Yb^+$ and some other ions are $^{133}Ba^+$). In yet additional embodiments, the group 106 of trapped ions may include various isotopes of the same species (e.g., different isotopes of Yb, different isotopes of Ba). The ions in the group 106 of trapped ions are individually addressed with separate laser beams. The classical computer 102 includes a central processing unit (CPU), memory, and support circuits (or I/O). The memory is connected to the CPU, and may be one or more of a readily available memory, such as a read-only memory (ROM), a random access memory (RAM), floppy disk, hard disk, or any other form of digital storage, local or remote. Software instructions, algorithms and data can be coded and stored within the memory for instructing the CPU. The support circuits (not shown) are also connected to the CPU for supporting the processor in a conventional manner. The support circuits may include conventional cache, power supplies, clock circuits, input/output circuitry, subsystems, and the like.

An imaging objective 108, such as an objective lens with a numerical aperture (NA), for example, of 0.37, collects fluorescence along the Y-axis from the ions and maps each ion onto a multi-channel photo-multiplier tube (PMT) 110 for measurement of individual ions. Non-copropagating Raman laser beams from a laser 112, which are provided along the X-axis, perform operations on the ions. A diffractive beam splitter 114 creates an array of static Raman beams 116 that are individually switched using a multi-channel acousto-optic modulator (AOM) 118 and is configured to selectively act on individual ions. A global Raman laser beam 120 illuminates all ions at once. In some embodiments, individual Raman laser beams (not shown) each illuminate individual ions. The system controller (also referred to as a "RF controller") 104 controls the AOM 118 and thus controls laser pulses to be applied to trapped ions in the group 106 of trapped ions. The system controller 104 includes a central processing unit (CPU) 122, a read-only memory (ROM) 124, a random access memory (RAM) 126, a storage unit 128, and the like. The CPU 122 is a processor of the system controller 104. The ROM 124 stores various programs and the RAM 126 is the working memory for various programs and data. The storage unit 128 includes a nonvolatile memory, such as a hard disk drive (HDD) or a flash memory, and stores various programs even if power is turned off. The CPU 122, the ROM 124, the RAM 126, and the storage unit 128 are interconnected via a bus 130. The system controller 104 executes a control program which is stored in the ROM 124 or the storage unit 128 and uses the RAM 126 as a working area. The control program will include software applications that include program code that may be executed by processor in order to perform various functionalities associated with receiving and analyzing data and controlling any and all aspects of the methods and hardware used to create the ion trap quantum computer system 100 discussed herein.

Figure 2:
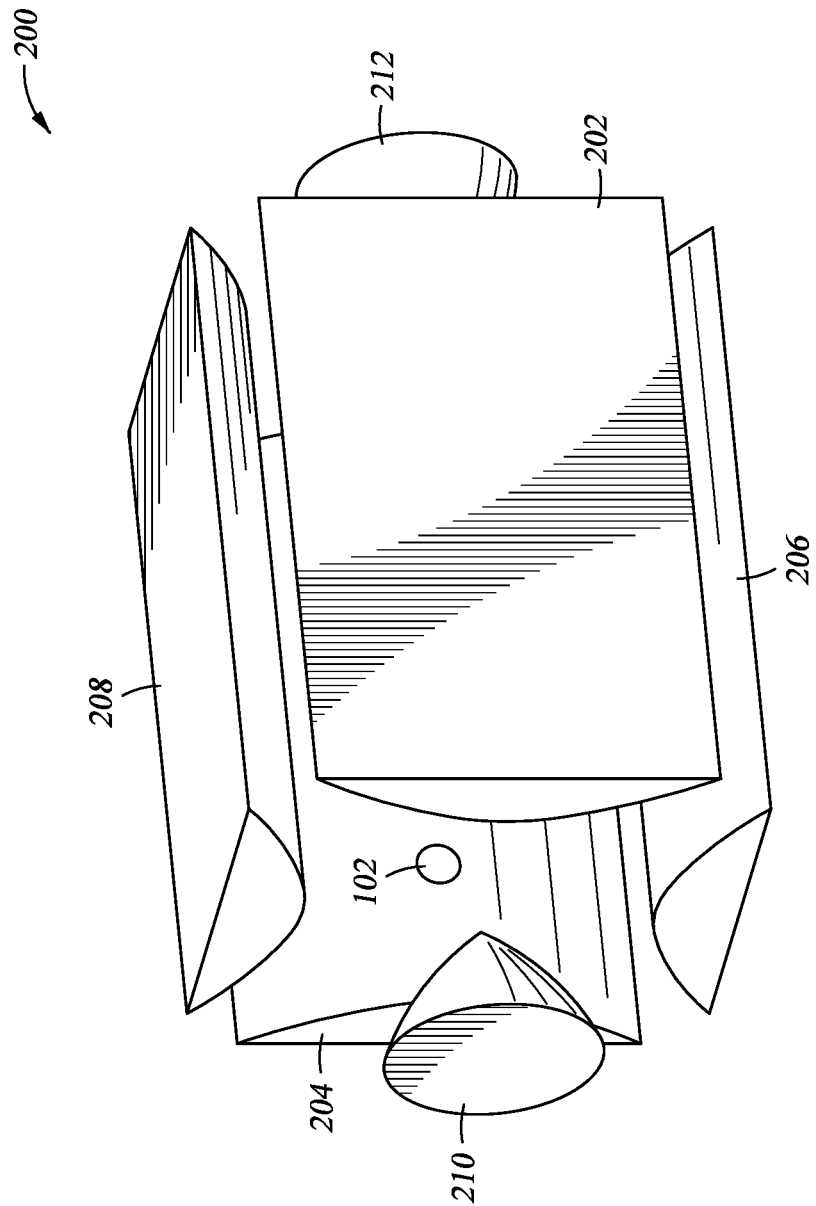
FIG. 2 depicts a schematic view of an ion trap for confining ions in a group according to one embodiment.

FIG. 2 depicts a schematic view of an ion trap 200 (also referred to as a Paul trap) for confining ions in the group 106 according to one embodiment. The confining potential is exerted by both static (DC) voltage and radio frequency (RF) voltages. A static (DC) voltage $V_S$ is applied to end-cap electrodes 210 and 212 to confine the ions along the Z-axis (also referred to as an "axial direction" or a "longitudinal direction"). The ions in the group 106 are nearly evenly distributed in the axial direction due to the Coulomb interaction between the ions. In some embodiments, the ion trap 200 includes four hyperbolically-shaped electrodes 202, 204, 206, and 208 extending along the Z-axis.

During operation, a sinusoidal voltage $V_1$ (with an amplitude $V_{RF}/2$) is applied to an opposing pair of the electrodes 202, 204 and a sinusoidal voltage $V_2$ with a phase shift of 180° from the sinusoidal voltage $V_1$ (and the amplitude $V_{RF}/2$) is applied to the other opposing pair of the electrodes 206, 208 at a driving frequency $\omega_{RF}$, generating a quadrupole potential. In some embodiments, a sinusoidal voltage is only applied to one opposing pair of the electrodes 202, 204, and the other opposing pair 206, 208 is grounded. The quadrupole potential creates an effective confining force in the X-Y plane perpendicular to the Z-axis (also referred to as a "radial direction" or "transverse direction") for each of the trapped ions, which is proportional to a distance from a saddle point (i.e., a position in the axial direction (Z-direction)) at which the RF electric field vanishes. The motion in the radial direction (i.e., direction in the X-Y plane) of each ion is approximated as a harmonic oscillation (referred to as secular motion) with a restoring force towards the saddle point in the radial direction and can be modeled by spring constants $k_x$ and $k_y$, respectively, as is discussed in greater detail below. In some embodiments, the spring constants in the radial direction are modeled as equal when the quadrupole potential is symmetric in the radial direction. However, undesirably in some cases, the motion of the ions in the radial direction may be distorted due to some asymmetry in the physical trap configuration, a small DC patch potential due to inhomogeneity of a surface of the electrodes, or the like and due to these and other external sources of distortion the ions may lie off-center from the saddle points.

Figure 3:
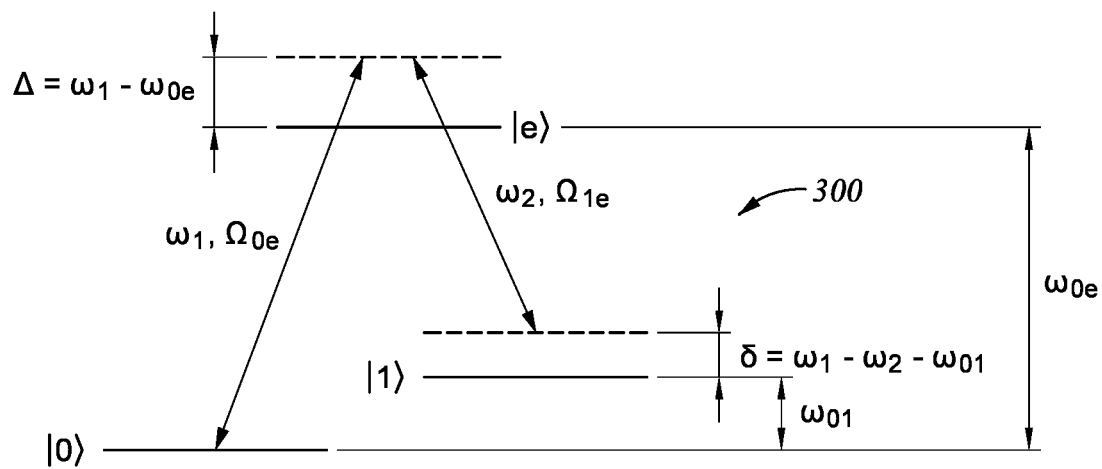
FIG. 3 depicts a schematic energy diagram of each ion in a group of trapped ions according to one embodiment.

FIG. 3 depicts a schematic energy diagram 300 of each ion in the group 106 of trapped ions according to one embodiment. Each ion in the group 106 of trapped ions is an ion having a nuclear spin I and an electron spin S such that a difference between the nuclear spin I and the electron spin S is zero. In one example, each ion may be a positive Ytterbium ion, $^{171}Yb^+$, which has a nuclear spin I=½ and the $^2S_{1/2}$ hyperfine states (i.e., two electronic states) with an energy split corresponding to a frequency difference (referred to as a "carrier frequency") of $\omega_{01}/2\pi=12.642812$ GHz. In other examples, each ion may be a positive barium ion $^{133}Ba^+$, a positive cadmium ion $^{111}Cd^+$ or $^{113}Cd^+$, which all have a nuclear spin I=½ and the $^2S_{1/2}$ hyperfine states. A qubit is formed with the two hyperfine states, denoted as $|0\rangle$ and $|1\rangle$, where the hyperfine ground state (i.e., the lower energy state of the $^2S_{1/2}$ hyperfine states) is chosen to represent $|0\rangle$. Hereinafter, the terms "hyperfine states," "internal hyperfine states," and "qubits" may be interchangeably used to represent $|0\rangle$ and $|1\rangle$. Each ion may be cooled (i.e., kinetic energy of the ion may be reduced) to near the motional ground state $|0\rangle_m$ for any motional mode m with no phonon excitation (i.e., $n_{ph}=0$) by known laser cooling methods, such as Doppler cooling or resolved sideband cooling, and then the qubit state prepared in the hyperfine ground state $|0\rangle$ by optical pumping. Here, $|0\rangle$ represents the individual qubit state of a trapped ion whereas $|0\rangle_m$ with the subscript m denotes the motional ground state for a motional mode m of a group 106 of trapped ions.

An individual qubit state of each trapped ion may be manipulated by, for example, a mode-locked laser at 355 nanometers (nm) via the excited $^2P_{1/2}$ level (denoted as $|e\rangle$). As shown in FIG. 3, a laser beam from the laser may be split into a pair of non-copropagating laser beams (a first laser beam with frequency $\omega_1$ and a second laser beam with frequency $\omega_2$) in the Raman configuration, and detuned by a one-photon transition detuning frequency $\Delta=\omega_1-\omega_{0e}$ with respect to the transition frequency $\omega_{0e}$ between $|0\rangle$ and $|e\rangle$, as illustrated in FIG. 3. A two-photon transition detuning frequency $\delta$ includes adjusting the amount of energy that is provided to the trapped ion by the first and second laser beams, which when combined is used to cause the trapped ion to transfer between the hyperfine states $|0\rangle$ and $|1\rangle$. When the one-photon transition detuning frequency $\Delta$ is much larger than a two-photon transition detuning frequency (also referred to simply as "detuning frequency") $\delta=\omega_1-\omega_2-\omega_{01}$ (hereinafter denoted as $\pm\mu$, $\mu$ being a positive value), single-photon Rabi frequencies $\Omega_{0e}(t)$ and $\Omega_{1e}(t)$ (which are time-dependent, and are determined by amplitudes and phases of the first and second laser beams), at which Rabi flopping between states $|0\rangle$ and $|e\rangle$ and between states $|1\rangle$ and $|e\rangle$ respectively occur, and a spontaneous emission rate from the excited state $|e\rangle$, Rabi flopping between the two hyperfine states $|0\rangle$ and $|1\rangle$ (referred to as a "carrier transition") is induced at the two-photon Rabi frequency $\Omega(t)$. The two-photon Rabi frequency $\Omega(t)$ has an intensity (i.e., absolute value of amplitude) that is proportional to $\omega_{0e}\Omega_{1e}/2\Delta$, where $\Omega_{0e}$ and $\Omega_{1e}$ are the single-photon Rabi frequencies due to the first and second laser beams, respectively. Hereinafter, this set of non-propagating laser beams in the Raman configuration to manipulate internal hyperfine states of qubits (qubit states) may be referred to as a "composite pulse" or simply as a "pulse," and the resulting time-dependent pattern of the two-photon Rabi frequency $\Omega(t)$ may be referred to as an "amplitude" of a pulse or simply as a "pulse," which are illustrated and further described below. The detuning frequency $\delta=\omega_1-\omega_2-\omega_{01}$ may be referred to as detuning frequency of the composite pulse or detuning frequency of the pulse. The amplitude of the two-photon Rabi frequency $\Omega(t)$, which is determined by amplitudes of the first and second laser beams, may be referred to as an "amplitude" of the composite pulse.

It should be noted that the particular atomic species used in the discussion provided herein is just one example of atomic species which have stable and well-defined two-level energy structures when ionized and an excited state that is optically accessible, and thus is not intended to limit the possible configurations, specifications, or the like of an ion trap quantum computer according to the present disclosure. For example, other ion species include alkaline earth metal ions ($Be^+$, $Ca^+$, $Sr^+$, $Mg+$, and $Ba^+$) or transition metal ions ($Zn^+$, $Hg^+$, $Cd^+$).

Figure 4:
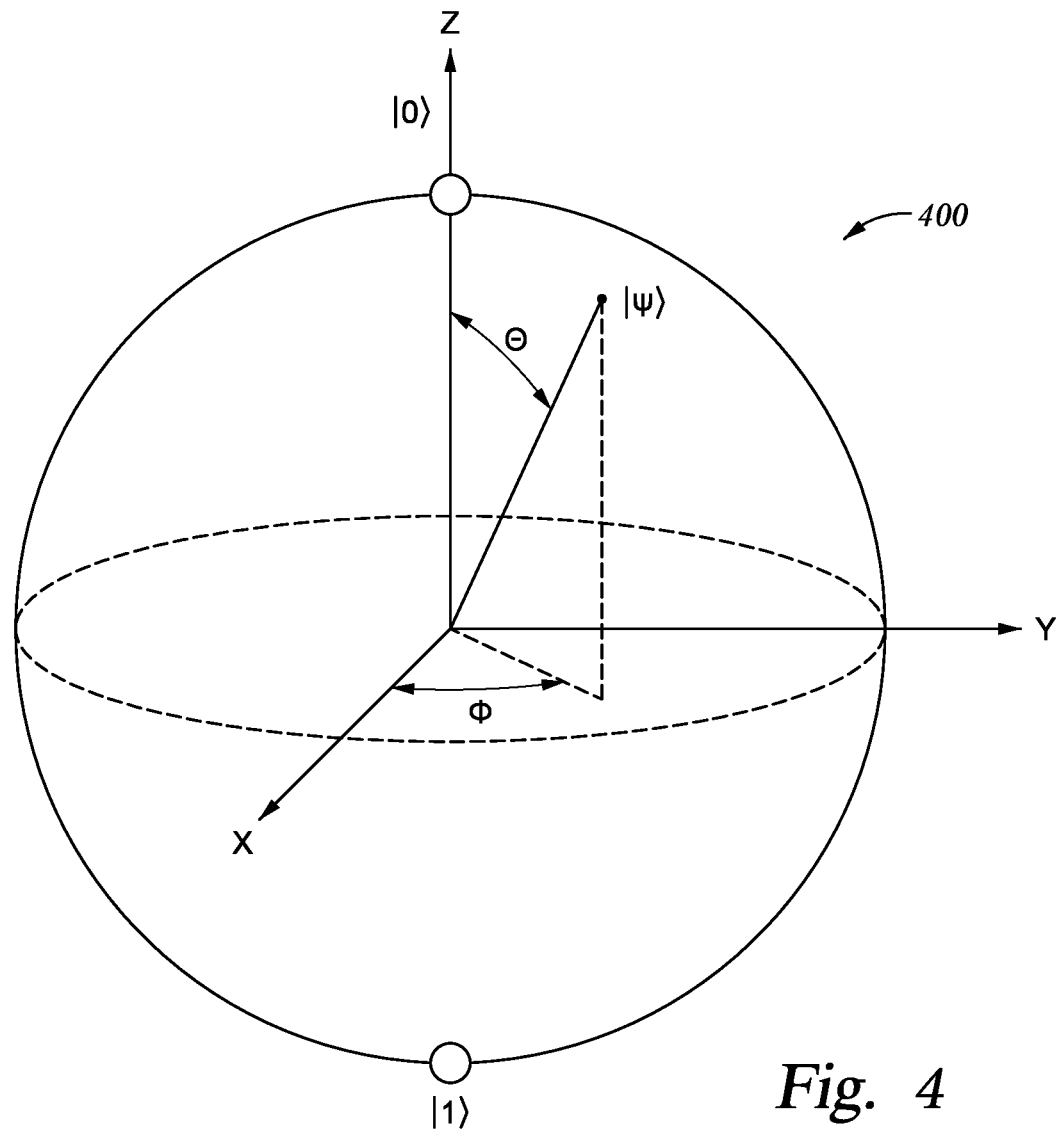
FIG. 4 depicts a qubit state of an ion represented as a point on a surface of the Bloch sphere.

FIG. 4 is provided to help visualize a qubit state of an ion is represented as a point on a surface of the Bloch sphere 400 with an azimuthal angle $\phi$ and a polar angle $\theta$. Application of the composite pulse as described above, causes Rabi flopping between the qubit state $|0\rangle$ (represented as the north pole of the Bloch sphere) and $|1\rangle$ (the south pole of the Bloch sphere) to occur. Adjusting time duration and amplitudes of the composite pulse flips the qubit state from $|0\rangle$ to $|1\rangle$ (i.e., from the north pole to the south pole of the Bloch sphere), or the qubit state from $|1\rangle$ to $|0\rangle$ (i.e., from the south pole to the north pole of the Bloch sphere). This application of the composite pulse is referred to as a "$\pi$-pulse". Further, by adjusting time duration and amplitudes of the composite pulse, the qubit state $|0\rangle$ may be transformed to a superposition state $|0\rangle+|1\rangle$, where the two single-qubit states $|0\rangle$ and $|1\rangle$ are added and equally-weighted in-phase (a normalization factor of the superposition state is omitted hereinafter for convenience) and the qubit state $|1\rangle$ to a superposition state $|0\rangle-|1\rangle$, where the two qubit states $|0\rangle$ and $|1\rangle$ are added equally-weighted but out of phase. This application of the composite pulse is referred to as a "$\pi/2$-pulse". More generally, a superposition of the two qubit states $|0\rangle$ and $|1\rangle$ that are added and equally-weighted is represented by a point that lies on the equator of the Bloch sphere. For example, the superposition states $|0\rangle\pm|1\rangle$ correspond to points on the equator with the azimuthal angle $\phi$ being zero and $\pi$, respectively. The superposition states that correspond to points on the equator with the azimuthal angle $\phi$ are denoted as $|0\rangle+e^{i\phi}|1\rangle$ (e.g., $|0\rangle\pm i|1\rangle$ for $\phi=\pm\pi/2$). Transformation between two points on the equator (i.e., a rotation about the Z-axis on the Bloch sphere) can be implemented by shifting phases of the composite pulse.

II. Entanglement Formation

Figure 5A:
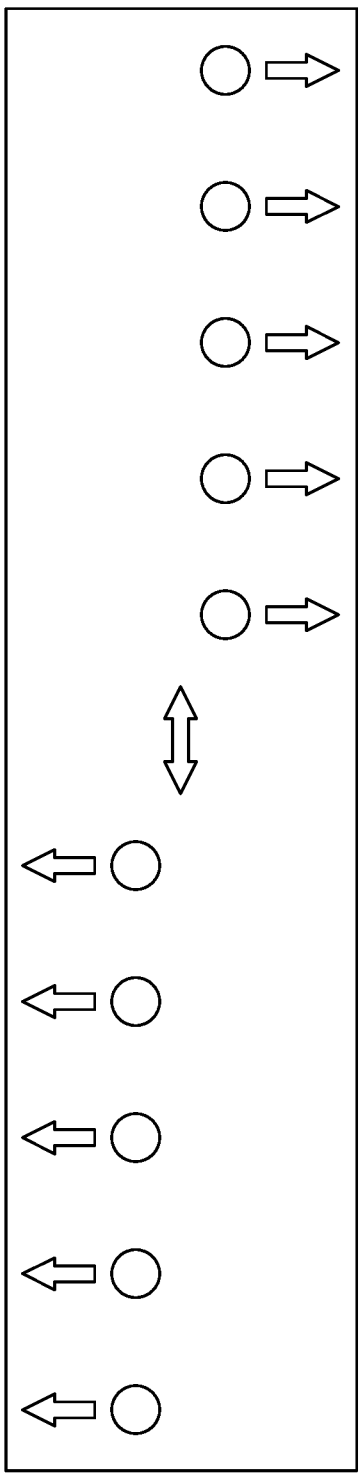
FIGS. 5A, 5B, and 5C depict a few schematic collective transverse motional mode structures of a group of five trapped ions.
Figure 5B:
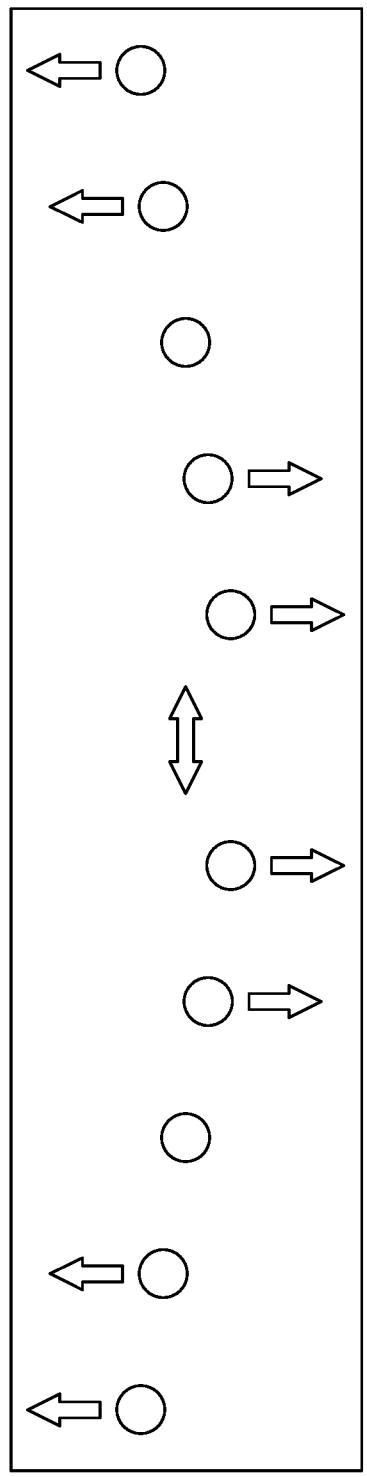
Figure 5C:
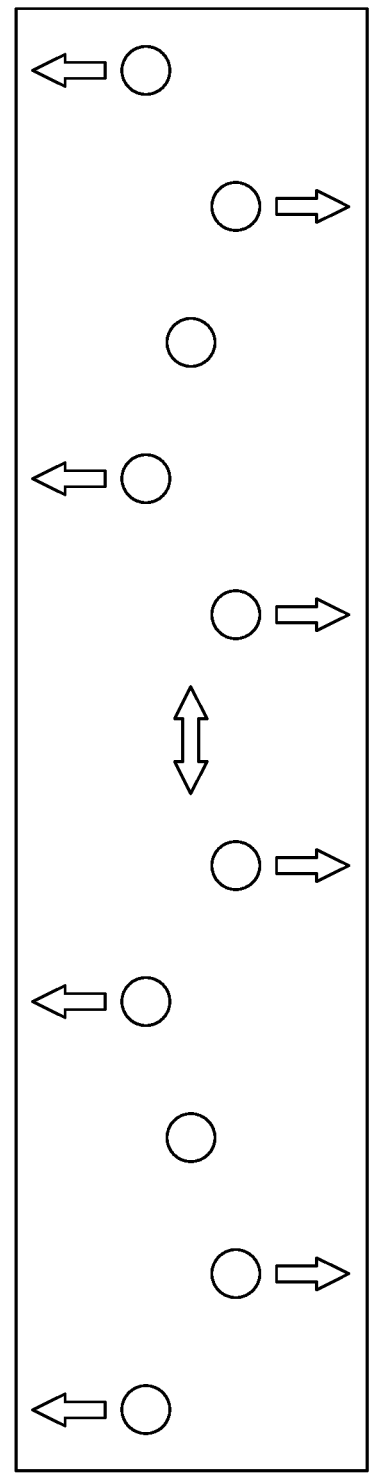

FIGS. 5A, 5B, and 5C depict a few schematic structures of collective transverse motional modes (also referred to simply as "motional mode structures") of a group 106 of five trapped ions, for example. Here, the confining potential due to a static voltage $V_S$ applied to the end-cap electrodes 210 and 212 is weaker compared to the confining potential in the radial direction. The collective motional modes of the group 106 of trapped ions in the transverse direction are determined by the Coulomb interaction between the trapped ions combined with the confining potentials generated by the ion trap 200. The trapped ions undergo collective transversal motions (referred to as "collective transverse motional modes," "collective motional modes," or simply "motional modes"), where each mode has a distinct energy (or equivalently, a frequency) associated with it. A motional mode having the m-th lowest energy is hereinafter referred to as $|n_{ph}\rangle_m$, where $n_{ph}$ denotes the number of motional quanta (in units of energy excitation, referred to as phonons) in the motional mode, and the number of motional modes M in a given transverse direction is equal to the number of trapped ions in the group 106. FIGS. 5A-5C schematically illustrates examples of different types of collective transverse motional modes that may be experienced by five trapped ions that are positioned in a group 106. FIG. 5A is a schematic view of a common motional mode $|n_{ph}\rangle_M$ having the highest energy, where M is the number of motional modes. In the common motional mode $|n\rangle_M$, all ions oscillate in phase in the transverse direction. FIG. 5B is a schematic view of a tilt motional mode $|n_{ph}\rangle_{M-1}$ which has the second highest energy. In the tilt motional mode, ions on opposite ends move out of phase in the transverse direction (i.e., in opposite directions). FIG. 5C is a schematic view of a higher-order motional mode $|n_{ph}\rangle_{M-3}$ which has a lower energy than that of the tilt motional mode $|n_{ph}\rangle_{M-1}$, and in which the ions move in a more complicated mode pattern.

It should be noted that the particular configuration described above is just one among several possible examples of a trap for confining ions according to the present disclosure and does not limit the possible configurations, specifications, or the like of traps according to the present disclosure. For example, the geometry of the electrodes is not limited to the hyperbolic electrodes described above. In other examples, a trap that generates an effective electric field causing the motion of the ions in the radial direction as harmonic oscillations may be a multi-layer trap in which several electrode layers are stacked and an RF voltage is applied to two diagonally opposite electrodes, or a surface trap in which all electrodes are located in a single plane on a chip. Furthermore, a trap may be divided into multiple segments, adjacent pairs of which may be linked by shuttling one or more ions, or coupled by photon interconnects. A trap may also be an array of individual trapping regions arranged closely to each other on a micro-fabricated ion trap chip. In some embodiments, the quadrupole potential has a spatially varying DC component in addition to the RF component described above.

Figure 6A:
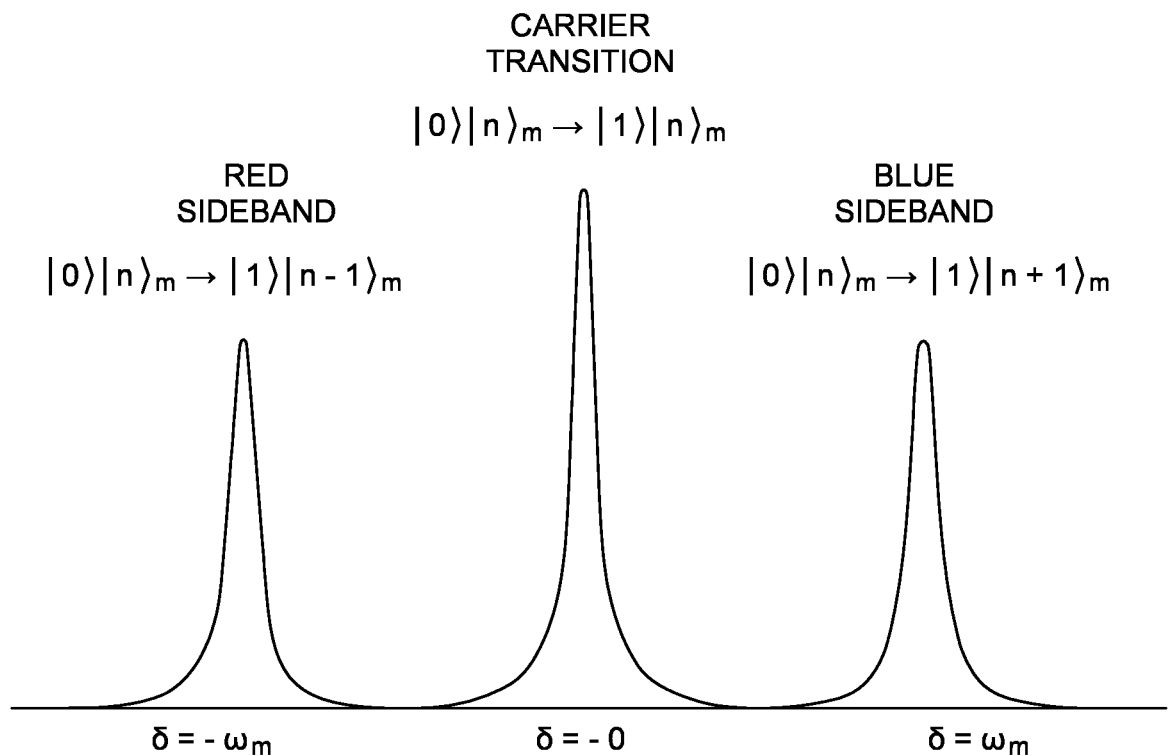
FIGS. 6A and 6B depict schematic views of motional sideband spectrum of each ion and a motional mode according to one embodiment.
Figure 6B:
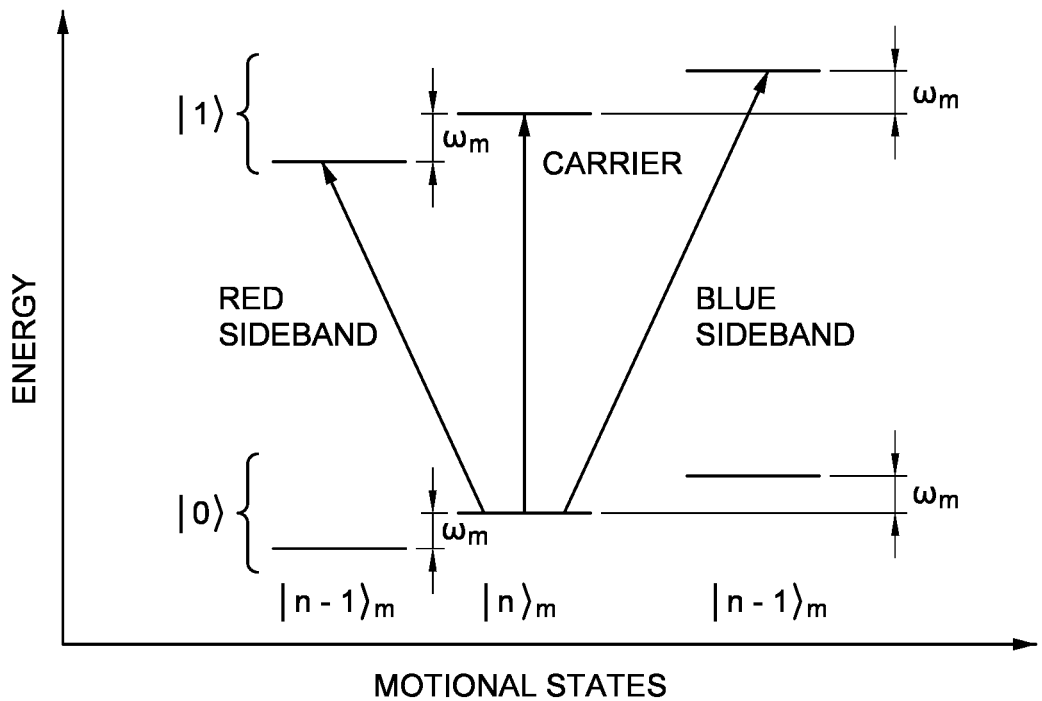

In an ion trap quantum computer, the motional modes may act as a data bus to mediate entanglement between two qubits and this entanglement is used to perform an XX gate operation. That is, each of the two qubits is entangled with the motional modes, and then the entanglement is transferred to an entanglement between the two qubits by using motional sideband excitations, as described below. FIGS. 6A and 6B schematically depict views of a motional sideband spectrum for an ion in the group 106 in a motional mode $|n_{ph}\rangle_M$ having frequency $\omega_m$ according to one embodiment. As illustrated in FIG. 6B, when the detuning frequency of the composite pulse is zero (i.e., a frequency difference between the first and second laser beams is tuned to the carrier frequency, $\delta=\omega_1-\omega_2-\omega_{01}=0$), simple Rabi flopping between the qubit states $|0\rangle$ and $|1\rangle$ (carrier transition) occurs. When the detuning frequency of the composite pulse is positive (i.e., the frequency difference between the first and second laser beams is tuned higher than the carrier frequency, $\delta=\omega_1-\omega_2-\omega_{01}=\mu>0$, referred to as a blue sideband), Rabi flopping between combined qubit-motional states $|0\rangle|n_{ph}\rangle_m$ and $|1\rangle|n_{ph}+1\rangle$ occurs (i.e., a transition from the m-th motional mode with n-phonon excitations denoted by $|n_{ph}\rangle_m$ to the m-th motional mode with $(n_{ph}+1)$-phonon excitations denoted by $|n_{ph}+1\rangle_m$ occurs when the qubit state $|0\rangle$ flips to $|1\rangle$). When the detuning frequency of the composite pulse is negative (i.e., the frequency difference between the first and second laser beams is tuned lower than the carrier frequency by the frequency $\omega_m$ of the motional mode $|n_{ph}\rangle_m$, $\delta=\omega_1-\omega_2-\omega_{01}=-\mu<0$, referred to as a red sideband), Rabi flopping between combined qubit-motional states $|0\rangle|n_{ph}\rangle_m$ and $|1\rangle|n_{ph}-1\rangle_m$ occurs (i.e., a transition from the motional mode $|n_{ph}\rangle_m$ to the motional mode $|n_{ph}-1\rangle_m$ with one less phonon excitations occurs when the qubit state $|0\rangle$ flips to $|1\rangle$). A $\pi/2$-pulse on the blue sideband applied to a qubit transforms the combined qubit-motional state $|0\rangle|n_{ph}\rangle_m$ into a superposition of $|0\rangle|n_{ph}\rangle_m$ and $|1\rangle|n_{ph}+1\rangle_m$. A $\pi/2$-pulse on the red sideband applied to a qubit transforms the combined qubit-motional $|0\rangle|n_{ph}\rangle_m$ into a superposition of $|0\rangle|n_{ph}\rangle_m$ and $|1\rangle|n_{ph}-1\rangle_m$. When the two-photon Rabi frequency $\Omega(t)$ is smaller as compared to the detuning frequency $\delta=\omega_1-\omega_2-\omega_{01}=\pm\mu$, the blue sideband transition or the red sideband transition may be selectively driven. Thus, a qubit can be entangled with a desired motional mode by applying the right type of pulse, such as a $\pi/2$-pulse, which can be subsequently entangled with another qubit, leading to an entanglement between the two qubits that is needed to perform an XX-gate operation in an ion trap quantum computer.

By controlling and/or directing transformations of the combined qubit-motional states as described above, an XX-gate operation may be performed on two qubits (i-th and j-th qubits). In general, the XX-gate operation (with maximal entanglement) respectively transforms two-qubit states $|0\rangle_i|0\rangle_j$, $|0\rangle_i|1\rangle_j$, $|1\rangle_i|0\rangle_j$, and $|1\rangle_i|1\rangle_j$ as follows:

$$|0\rangle_i|0\rangle_j \to |0\rangle_i|0\rangle_j - i|1\rangle_i|1\rangle_j$$

$$|0\rangle_i|1\rangle_j \to |0\rangle_i|1\rangle_j - i|1\rangle_i|0\rangle_j$$

$$|1\rangle_i|0\rangle_j \to -i|0\rangle_i|1\rangle_j + |1\rangle_i|0\rangle_j$$

$$|1\rangle_i|1\rangle_j \to -i|0\rangle_i|0\rangle_j + |1\rangle_i|1\rangle_j$$

For example, when the two qubits (i-th and j-th qubits) are both initially in the hyperfine ground state $|0\rangle$ (denoted as $|0\rangle_i|0\rangle_j$) and subsequently a $\pi/2$-pulse on the blue sideband is applied to the i-th qubit, the combined state of the i-th qubit and the motional mode $|0\rangle_i|n_{ph}\rangle_m$ is transformed into a superposition of $|0\rangle_i|n_{ph}\rangle_m$ and $|1\rangle_i|n_{ph}+1\rangle_m$, and thus the combined state of the two qubits and the motional mode is transformed into a superposition of $|0\rangle_i|0\rangle_j|n_{ph}\rangle_m$ and $|1\rangle_i|0\rangle_j|n_{ph}+1\rangle_m$. When a $\pi/2$-pulse on the red sideband is applied to the j-th qubit, the combined state of the j-th qubit and the motional mode $|0\rangle_j|n_{ph}\rangle_m$ is transformed to a superposition of $|0\rangle_j|n_{ph}\rangle_m$ and $|1\rangle_j|n_{ph}-1\rangle_m$ and the combined state $|0\rangle_j|k_{ph}+1\rangle_m$ is transformed into a superposition of $|0\rangle_j|n_{ph}+1\rangle_m$ and $|1\rangle_j|n_{ph}\rangle_m$.

Thus, applications of a $\pi/2$-pulse on the blue sideband on the i-th qubit and a $\pi/2$-pulse on the red sideband on the j-th qubit may transform the combined state of the two qubits and the motional mode $|0\rangle_i|0\rangle_j|n_{ph}\rangle_m$ into a superposition of $|0\rangle_i|0\rangle_j|n_{ph}\rangle_m$ and $|1\rangle_i|1\rangle_j|n_{ph}\rangle_m$, the two qubits now being in an entangled state. For those of ordinary skill in the art, it should be clear that two-qubit states that are entangled with motional mode having a different number of phonon excitations from the initial number of phonon excitations $n_{ph}$ (i.e., $|1\rangle_i|0\rangle_j|n_{ph}+1\rangle_m$ and $|0\rangle_i|1\rangle_j|n_{ph}-1\rangle_m$) can be removed by a sufficiently complex pulse sequence, and thus the combined state of the two qubits and the motional mode after the XX-gate operation may be considered disentangled as the initial number of phonon excitations $n_{ph}$ in the m-th motional mode stays unchanged at the end of the XX-gate operation. Thus, qubit states before and after the XX-gate operation will be described below generally without including the motional modes.

More generally, the combined state of i-th and j-th qubits transformed by the application of pulses on the sidebands for duration $\tau$ (referred to as a "gate duration"), having amplitudes $\omega^{(i)}$ and $\Omega^{(j)}$ and detuning frequency $\mu$, can be described in terms of an entangling interaction $\chi^{(i,j)}(\tau)$ as follows:

$$|0\rangle_i|0\rangle_j \to \cos(2\chi^{(i,j)}(\tau))|0\rangle_i|0\rangle_j - i\sin(2\chi^{(i,j)}(\tau))|1\rangle_i|1\rangle_j$$

$$|0\rangle_i|1\rangle_j \to \cos(2\chi^{(i,j)}(\tau))|0\rangle_i|1\rangle_j - i\sin(2\chi^{(i,j)}(\tau))|1\rangle_i|0\rangle_j$$

$$|1\rangle_i|0\rangle_j \to -i\sin(2\chi^{(i,j)}(\tau))|0\rangle_i|1\rangle_{nj} + \cos(2\chi^{(i,j)}(\tau))|1\rangle_i|0\rangle_j$$

$$|1\rangle_i|1\rangle_j \to -i\sin(2\chi^{(i,j)}(\tau))|0\rangle_i|0\rangle_{nj} + \cos(2\chi^{(i,j)}(\tau))|1\rangle_i|1\rangle_j$$

where, $$\chi^{(i,j)}(\tau) =$$

$$-4\sum_{m=1}^{M} \eta_m^{(i)} \eta_m^{(j)} \int_0^\tau dt_2 \int_0^{t_2} dt_1 \Omega^{(i)}(t_2)\Omega^{(j)}(t_1)\cos(\mu t_2)\cos(\mu t_1)\sin[\omega_m(t_2-t_1)]$$

and $\eta_m^{(i)}$ is the Lamb-Dicke parameter that quantifies the coupling strength between the i-th ion and the m-th motional mode having the frequency $\omega_m$, and M is the number of the motional modes (equal to the number N of ions in the group 106).

The entanglement interaction between two qubits described above can be used to perform an XX-gate operation. The XX-gate operation (XX gate) along with single-qubit operations (R gates) forms a set of gates {R, XX} that can be used to build a quantum computer that is configured to perform desired computational processes. Among several known sets of logic gates by which any quantum algorithm can be decomposed, a set of logic gates, commonly denoted as {R, XX}, is native to a quantum computing system of trapped ions described herein. Here, the R gate corresponds to manipulation of individual qubit states of trapped ions, and the XX gate (also referred to as an "entangling gate") corresponds to manipulation of the entanglement of two trapped ions.

To perform an XX-gate operation between i-th and j-th qubits, pulses that satisfy the condition $x^{(i,j)}(\tau)=\theta^{(i,j)}$ ($0<\theta^{(i,j)}\leq\pi/8$) (i.e., the entangling interaction $\chi^{(i,j)}(\tau)$ has a desired value $\theta^{(i,j)}$, referred to as condition for a non-zero entanglement interaction) are constructed and applied to the i-th and the j-th qubits. The transformations of the combined state of the i-th and the j-th qubits described above corresponds to the XX-gate operation with maximal entanglement when $\theta^{(i,j)}=\pi/8$. Amplitudes $\Omega^{(i)}(t)$ and $\Omega^{(j)}(t)$ of the pulses to be applied to the i-th and the j-th qubits are control parameters that can be adjusted to ensure a non-zero tunable entanglement of the i-th and the j-th qubits to perform a desired XX gate operation on i-th and j-th qubits.

III. Quantum Simulation

In a quantum computing system, a quantum computer is a domain-specific accelerator (also referred to as a "quantum processor" hereinafter) that may be able to accelerate certain computational tasks beyond the reach of classical computers. Examples of such computational tasks include quantum molecular dynamics (MD) simulations of a system having particles that interact with one another via short-range and long-range interactions. Examples of such MD simulations include studies of biological materials in aqueous solutions and simulating various aspects of protein folding. The dynamics of such a system is dictated by the energetics of the system and the primary contribution to the energies of the system comes from the Coulomb interaction among particles. Thus, methods for computing inter-particle interaction energies due to the Coulomb interaction among particles are described herein.

It should be noted that the particular example embodiments described herein are just some possible examples of a quantum computing system according to the present disclosure and do not limit the possible configurations, specifications, or the like of quantum computer systems according to the present disclosure.

The embodiments described herein provide methods for an accurate quantum simulation of an infinite system. A naive approach would involve calculating the energetics on the infinitely many quantum particles. Since a simulation is performed in a finite time and any computational system only has a finite memory, a simulation of a truly infinite system cannot be performed. One way to get around this problem is to select a representative volume of the infinite system and to extend it spatially in three dimensions by making copies of it. Imposing periodic boundary condition in this manner enables an approximate simulation of the infinite system with a finite memory and simulation time.

Crucially, to approximate a truly infinite system using periodic boundary conditions, the representative volume (also known as a unit cell) needs to be sufficiently big. If the unit cell is too small, finite size effects come into play, leading to an inaccurate simulation. One way to check that the unit cell is sufficiently big is to simulate a sequence of progressively larger unit cell, until a (thermodynamic) variable of interest converges. This is expected to happen at the thermodynamic limit. With a tool to simulate a system of a given size perfectly, systems in increasing sizes can be simulated, until a convergence in the variable of interest is reached as an accurately simulated result of an infinite system.

The known methods to simulate quantum systems are however not perfect and they incur error. The embodiments described herein thus construct a tool that can simulate a unit cell of any size with a fixed, sufficiently small, absolute error. This way, the unit cell can be scaled up and simulated with no more than a pre-specified amount of error, being able to unambiguously determine the convergence in the variables of interest. Hence analysis of the computational complexity required for the bounded-error, unit-cell simulations with varying sizes is described below.

III.A System Specification

In the quantum molecular dynamics (MD) simulations, a bulk material is typically modeled as an infinite system in which a finite system (referred to as a "unit cell") of $\eta$ interacting particles is duplicated with periodic boundary conditions imposed. The $\eta$ interacting particles may have long-range interactions (e.g., Coulomb interaction) with one another.

The system of the $\eta$ interacting particles in a unit cell of a cubic shape with an edge length of L evolves in time according to a Hamiltonian, H=T+V, that is a sum of the kinetic term T, $$T = \Sigma_{i=0}^{\eta-1} \frac{p_i^2}{2m_i}, \tag{1}$$

where $p_i$ and $m_i$ are the momentum and mass of i-th particle, and the Coulomb potential term V, $$V = \Sigma_{t\in\mathbb{Z}^3} \Sigma_{\substack{i,j=0 \\ i\neq j \text{ when } t=0}}^{\eta-1} \frac{1}{2} \frac{q_i q_j}{|r_i - r_j + tL|}, \tag{2}$$

where $r_i$ and $r_j$ are the positions of i-th and j-th particles, respectively, $q_i$ and $q_j$ are charges of the i-th and j-th particles, respectively, and $t=(t_x, t_y, t_z)$ is a lattice vector of integer indices for each duplicated unit cell. The expectation values of the Hamiltonian H, the kinetic term T, and the Coulomb potential term V are total energy, kinetic energy, and Coulomb potential energy, respectively, of the system. The dynamics of the system of the η interacting particles for a time duration τ can be described by an evolution operator U(τ), $$U(\tau)=e^{iH\tau}=e^{i(T+V)\tau} \quad (3)$$

In the embodiments described herein, the time duration τ of the evolution operator U(τ) to be simulated is chosen to be scale as $\tau=O(\eta^{2/3})$. This choice is known in the art to be suitable for statistics neccesary for MD simulations.

For practical computation, the sum over lattice vectors t is bounded by a cutoff $t_c$ such that $|t_x|, |t_y|, |t_z| \leq t_c$. The number of particles inside the cutoff of $t_c$ among the η interacting particles in the cubit unit cell of size $L^3$ is given by $(2t_c+1)^3\eta$. An error $\epsilon_{truncation}$ incurred by this truncation, characterized by $t_c$, is given by $$\epsilon_{truncation} = \sum_{|t_x|,|t_y|,|t_z|>t_c} t \in \mathbb{Z}^3 \; \Sigma_{j,k=0}^{\eta-1} \frac{q_j q_k}{|r_j - r_k + tL|}. \quad (4)$$

III.B Suzuki-Trotter Approximation and Kinetic Terms

In the embodiments described herein, the evolution operator U(τ) is implemented using the Suzuki-Trotter approximation, known in the art, of 2 k-th order. That is, the evolution operator U(τ) is approximated as a repetition of an evolution operator $S_{2k}$ for a time step, δt, $$U(\tau) \approx (S_{2k})^r \quad (5)$$

where r is a sufficiently large number chosen such the time step, δt=τ/r is, small. The 2 k-th order evolution operator $S_{2k}$ in the Suzuki-Trotter approximation is defined recursively as $$S_{2k}=(S_{2k-2}(u_k t))^2 S_{2k-2}((1-4u_k)t)(S_{2k-2}(u_k t))^2, S_2(t)= e^{iTt/2}e^{iVt}e^{iTt/2} \quad (6)$$

with $u_k=1/(4-4^{1/(2k-1)})$. It should be noted that the evolution operator $S_{2k}$ is a series of kinetic terms of the form $e^{-iTt}$ and Couloumb potential terms of the form of $e^{-iVt}$.

In a simulation using a quantum computer, such as the system 100, a state ψ of the system of the η interacting particles is encoded into two quantum registers of a quantum processor, such as the group 106 of trapped ions. The first quantum register (referred to also as a "charge register") is formed of η qubits to encode the charges $q_i$ of the i-th particles (i=0, 1, 2, . . . , η−1) in a charge encoded state $|q_m\rangle$. The second quantum register (referred to also as a "position register") is formed of η sets of $\mathcal{O}(\log_2 N)$ qubits to encode the positions $r_i=(r_{i,x}, r_{i,y}, r_{i,z})$ of the i-th particles (i=0, 1, 2, . . . , η−1) in a position encoded state $|r_m\rangle = |r_{m,x}\rangle |r_{m,y}\rangle |r_{m,z}\rangle$ by discretizing the cubit unit cell with an edge length of L into sufficiently dense N cubic grids with an edge length Δ, where $N=L^3/\Delta^3$. The encoding of the charges $q_i$ into the charge register (i.e., transfering the charge register to the charge encoded state) and the encoding of the positions $r_i$ into the position register (i.e., transferring the position register to the position encoded state) can be each implemented by the application of a combination of gate operations to the charge register and the position register by a system controller, such as the system controller 104. In some embodiments, the combination of gate operations include single-qubit gate operations and two-qubit gate operations.

Thus, the state ψ of the system of the η interacting particles is represented by a tensor product of the charge register and the position register as $$\psi = \bigotimes_{m=0}^{\eta-1} |q_m\rangle \otimes |r_m\rangle = \bigotimes_{m=0}^{\eta-1} |q_m\rangle \otimes |r_{m,x}\rangle |r_{m,y}\rangle |r_{m,z}\rangle. \quad (7)$$

The state ψ of the system of the η interacting particles represented in the position basis above can be transformed in the momentum basis as $$\psi = \bigotimes_{m=0}^{\eta-1} |q_m\rangle \otimes \left(\sum_{p_m} e^{ip_m r_m} |p_m\rangle\right) = \bigotimes_{m=0}^{\eta-1} |q_m\rangle \otimes \left(\sum_{p_m} e^{ip_m r_m} |p_{m,x}\rangle |p_{m,y}\rangle |p_{m,z}\rangle\right), \quad (8)$$

using the quantum discrete Fourier transform Q, which involves application of a combination of gate operations to the position register by a system controller, such as the system controller 104. In some embodiments, the combination of gate operations include single-qubit gate operations and two-qubit gate operations.

The kinetic term exp(iTt) is a product of the kinetic terms exp($iT_i t$) for i-th particles (i=0, 1, 2, . . . , η−1), exp(iTt)=$\Pi_{j=0}^{\eta-1}$ exp($iT_j t$), and can be implemented exactly in the momentum basis as, $$\exp(iT_j t)\left[\bigotimes_{m=0}^{\eta-1} |q_m\rangle |p_m\rangle\right] = \exp\left(i\frac{p_j^2}{2m_j}t\right)\left[\bigotimes_{m=0}^{\eta-1} |q_m\rangle |p_m\rangle\right]. \quad (9)$$

Each of the kinetic terms exp($iT_i t$) can be implemented using the phase-kickback transformation, known in the art, which involves application of a combination of gate operations to the position register by a system controller, such as the system controller 104. In some embodiments, the combination of gate operations include single-qubit gate operations and two-qubit gate operations. Application of the kinetic term exp(iTt) for a time duration t shifts the phase of the first and second quantum registers (i.e., a phase shift operation) by the kinetic energies of the interacting particles multiplied by time duration t. Thus, the phase shift of the first and second quantum registers simulates the evolution of the system by the kinetic term T of the Hamiltonian H. Results of the simulation are encoded in the phase of the first and second quantum registers.

The quantum discrete Fourier transformation Q is defined according to $$Q^{\otimes \eta}\left[\bigotimes_{m=0}^{\eta-1} |q_m, p_m\rangle\right] = \left[\bigotimes_{m=0}^{\eta-1} \left(\sum_r e^{ip_m \cdot r} |q_m, r\rangle\right)\right], \quad (10)$$

and applied on the position register for all η particles to induce the bases change from the momentum-basis to the position basis.

As briefly discussed in Subsection III. B, calculation of the Coulomb potential terms requires summation of the long-range interactions of all pairs among the η interacting particles. The long-range interactions of all pairs may be directly summed, as described in Subsection III.C, or summed using the Ewald summation method, as described in Subsection III.D.

III.C Direct Sum of Coulomb Potential Terms

The Coulomb potential term $\exp(iVt)$ is a product of pair-wise Coulomb potential terms $\exp(iV_{jk}t)$ for pairs of particles j, k (=0, 1, 2, ..., $\eta-1$), $\exp(iVt)=\Pi_{j>k}\exp(iV_{jk}t)$, and can be implemented as a series of pair-wise Coulomb potential terms, $$\exp(iV_{jk}t)\left(\bigotimes_{m=0}^{\eta-1}|q_m,p_m\rangle\right) = \exp\left(i\sum_{k\in Z^3}\frac{q_jq_k}{|r_j-r_k+tL|}t\right)\bigotimes_{m=0}^{\eta-1}|q_m,r_m\rangle, \quad (11)$$

where j, k sum runs over pairs of the $\eta$ interacting particles. Each of the pair-wise Coulomb potential terms $\exp(iV_{jk}t)$ can be implemented using the phase-kickback transformation known in the art, which involves application of a combination of gate operations to the position register by a system controller, such as the system controller 104. In some embodiments, the combination of gate operations include single-qubit gate operations and two-qubit gate operations. Application of the Coulomb potential term $\exp(iVt)$ for a time duration t shifts the phase of the first and second quantum registers (i.e., a phase shift operation) by the Coulomb potential energies of the interacting particles multiplied by time duration t. Thus, the phase shift of the first and second quantum registers simulates the evolution of the system by the Coulomb potential term V of the Hamiltonian H. Results of the simulation are encoded in the phase of the first and second quantum registers. It should be noted that there are $O(\eta^2)$ pair-wise Coulomb potential terms $\exp(iV_{jk}t)$ in the Coulomb potential term $\exp(iVt)$, and thus the computational complexity of the summation increases as $O(\eta^2)$ as the number of interacting particles $\eta$ increases. Details of resources needed to compute the Coulomb potential term $\exp(iVt)$ are discussed in Subsection IV.A. The total gate complexity to compute the direct sum of the Coulomb potential terms is shown to scale as $\tilde{O}(\eta^{11/3+5/(6k)})$ according to the embodiments described herein. This shows improvement over the conventional method using plane-wave orbitals in the regime where the number of orbital scales as $\Omega(\eta^{1+5/(2k)})$.

III.D Quantum Ewald Sum of Coulomb Potential Terms

The pair-wise Coulomb potential terms $\exp(iV_{jk}t)$ for j-th and k-th particles (j, k=0, 1, 2, ..., $\eta-1$) can be summed more efficiently by the Ewald summation method, known in the art, reducing the computational complexity.

In the Ewald summation method, the Coulomb potential term V is divided into three parts: short-range interaction $V_{short}$, long-range interaction $V_{long}$, and self-energy $V_{self}$, $$V_{Ewald}=V_{short}+V_{long}-V_{self} \quad (12)$$

A charge distribution $\rho(r)$ at a position r in the unit cell, for example, a sum of $\eta$ point charges (each of which is described by a Dirac delta function $\delta(r-r_i)$), $$\rho(r)=\Sigma_{i=0}^{\eta-1}q_i\delta(r-r_i),$$

is replaced by a sum of a screened charge distribution $\rho^S$(r)(i.e., each point charge is smeared) and a cancelling charge distribution $\rho^L(r)$ to compensate for the screened charge distribution $\rho^S(r)$, given by $$\rho(r)=\rho^S(r)+\rho^L(r),$$

where $$\rho^S(r)=\Sigma_{i=0}^{\eta-1}q_i(\delta(r-r_i)-W_\alpha(r-r_i)),$$

with a screening function $W_\alpha(r-r_i)$. The screening function $W_\alpha(r-r_i)$ may be, for example, a Gaussian screen function, $$W_\alpha(r-r_i) = \left(\frac{\alpha}{\sqrt{\pi}}\right)^3 \exp(-\alpha^2|r-r_i|^2),$$

where the parameter $\alpha>0$ defines a width of the screening. The screened charge distribution $\rho^S(r)$ screens the interaction between point charges that are separated more than the parameter $\alpha$ (that is, the inter-particle interaction due to the screened charge distribution $\rho^S(r)$ is short-range) and subsequently leads to a rapid convergence in calculating inter-particle interaction energies due to the screened charge distribution $\rho^S(r)$. To compensate a difference between the contribution to the inter-particle interaction energies due to the screened charge distribution $\rho^S(r)$ and that of the (original) charge distribution $\rho(r)$, the cancelling charge distribution $\rho^L(r)$ having the same charge sign as the point charge, $$\rho^L(r)=\Sigma_{i=0}^{\eta-1}q_iW_\alpha(r-r_i),$$

is added. The inter-particle interaction due to the cancelling charge distribution $\rho^L(r)$ is long-range.

Thus, the short-range interaction $V_{short}$, the long-range interaction $V_{long}$, and the self-energy $V_{self}$ in the Couloumb potential term in the Ewald summation method, $V_{Ewald}$, are $$V_{short} = \sum_{k\in Z^3}\sum_{k,j=0;i\neq j}^{\eta-1}\frac{1}{2}\frac{q_iq_j}{|r_j-r_k+tL|}\text{erfc}(\alpha|r_j-r_k+tL|), \quad (13)$$

$$V_{long} = \sum_k \frac{1}{2}\frac{e^{-k^2/\alpha^2}}{k^2}\left|\sum_i q_i e^{ik\cdot r_i}\right|^2,$$

and $$V_{self} = \frac{\alpha}{\pi^{1/2}}\sum_{k=0}^{\eta-1} q_i^2, \quad (14)$$

where k is the reciprocal-space vector and "·" denotes the inner product between two vectors.

As discussed in Subsection III.A, the sum over the lattice vectors t is bounded by a cutoff $t_c$. Thus, the sum over reciprocal vectors k is truncated to a reciprocal cut-off $P_c$ such that errors in the short-range interaction $V_{short}$ and the long-range interaction $V_{long}$ shown in Equation (13) are each upper-bounded by $\delta$. In particular, the reciprocal cut-off $P_c$ is chosen to be $P_c \approx 2(-\ln(\delta))/\pi$. Using this truncation, the size of the summation of the short-range interaction $V_{short}$ and the size of the summation of the long-range interaction $V_{long}$ within an error of $\delta$ is optimized to $O(\eta^{3/2})$.

Using the decomposition of the Coulomb potential term V into the short-range interaction $V_{short}$, the long-range interaction $V_{long}$, and the self-energy $V_{self}$, the Couloumb potential term $\exp(iVt)$ can be decomposed as, $$\exp(iVt)=\exp(iV_{short}t)\exp(iV_{long}t)\exp(-iV_{self}t), \quad (15)$$

where the short-range interaction term $\exp(iV_{short}t)$, the long-range interaction term $\exp(iV_{long}t)$, and the self-energy term $\exp(iV_{self}t)$ can be implemented using the phase-kickback transformation known in the art, which involves application of a combination of gate operations to the position register by a system controller, such as the system controller 104. In some embodiments, the combination of gate operations include single-qubit gate operations and two-qubit gate operations. Application of the short-range interaction term $\exp(iV_{short}t)$, the long-range interaction term $\exp(iV_{long}t)$, and the self-energy term $\exp(iV_{self}t)$ for a time duration t shifts the phase of the first and second quantum registers (i.e., a phase shift operation) by the short-range interaction energies, the long-range interaction energies, and the self-energies of the interacting particles, respectively, multiplied by time duration t. Thus, the phase shift of the first and second quantum registers simulates the evolution of the system by the short-range interaction $V_{short}$, the long-range interaction $V_{long}$, and the self-energy $V_{self}$ in the Coulomb potential term V. Results of the simulation are encoded in the phase of the first and second quantum registers. The short-range interaction term $\exp(iV_{short}t)$ can be further decomposed as $$\exp(iV_{short}t) = \prod_{l \in \mathbb{Z}^3} \prod_{j>k} \exp(iV_{jk}^S t), \quad (16)$$

$$\exp(iV_{jk}^S t)\psi = \exp\left(i\frac{q_j q_k \operatorname{erfc}(\alpha|r_j - r_k + tL|)}{2|r_j - r_k + tL|}t\right)\psi.$$

The long-range interaction term $\exp(iV_{long}t)$ can be further decomposed as $$\exp(iV_{long}t) = \quad (17)$$

$$\prod_k \exp(iV_k^L t), \exp(iV_k^L t)\psi = \exp\left(i\frac{e^{-k^2/\alpha^2}}{2} \left|\sum_j q_j e^{ik\cdot r_j}\right|^2 t\right)\psi$$

and the self-energy potential term $\exp(iV_{self}t)$ can be further decomposed as $$\exp(-iV_{self}t)\psi = \exp\left(-i\frac{\alpha}{\pi^{1/2}} \sum_{j=0}^{\eta-1} q_j^2\right)\psi. \quad (18)$$

Details of resources needed to compute the Coulomb potential term $\exp(iVt)$ are discussed in Subsection IV.B. The total gate complexity to compute the direct sum of the Coulomb potential terms is shown to scale as $\tilde{O}(\eta^{19/6+5/(6k)})$ according to the embodiments described herein. This shows improvement over the conventional method using plane-wave orbitals in the regime where the number of orbital scales as $\Omega(\eta^{-1/2+5/(2k)})$.

IV Analysis

In this Section, error analysis and computational complexity in simulating the system of $\eta$ particles for a time duration τ, specifically those of the direct sum of the pair-wise Coulomb potential terms $V_{jk}$ described in Subsection IV.C and the quantum Ewald sum of the pair-wise Coulomb potential terms $V_{jk}$ described in Subsection IV.C are discussed.

More specifically, resources needed to approximate an evolution operator $U(\tau)=e^{iH\tau}$ under a target Hamiltonian $H=T+V$ by an evolution operator $\tilde{U}(\tau)=e^{i\tilde{H}\tau}$ by a finite-precision Hamitonian $\tilde{H}=\tilde{V}+\tilde{T}$ are computed, where $\tilde{T}$ is a finite-precision kinetic term and $\tilde{V}$ is a finite-precision Coulomb potential term. There are several error sources in this approximation. A first error source is due to the fact that positions $r_i$ and momentum $p_i$ of i-th particles (i=0, 1, 2, ..., η−1) are represented by a finite number of bits, and is referred to as a finite-precision error $\varepsilon_{FP}$. A second error source is due to the Suzuki-Trotter approximation of the finite-precision Hamiltonian $\tilde{H}$ and is referred to as a Suzuki-Trotter error $\varepsilon_{Trotter}$. A total error in the summation of the pair-wise Coulomb potential terms $\exp(iV_{jk}t)$ is then upper-bounded by $$\varepsilon_{DCS} = \|e^{iH\tau} - \tilde{S}_{2k}^r\| \leq \|e^{iH\tau} - e^{i\tilde{H}\tau}\| + \|e^{i\tilde{H}\tau} - \tilde{S}_{2k}^r\|, \quad (19)$$

where $\tilde{S}_{2k}$ denotes the evolution operator $S_{2k}$ shown in Equation (6) with the kinetic term T and the Coulomb potential term V replaced by the finite-precision kinetic term $\tilde{T}$ and the finite-precision Coulomb potential term $\tilde{V}$, respectively. The first term $\|e^{iH\tau} - e^{i\tilde{H}\tau}\|$ in the expansion in Equation (19) is the finite-precision error $\varepsilon_{FP}$ and may bounded as $$\varepsilon_{FP} = \|e^{iH\tau} - e^{i\tilde{H}\tau}\| = \tau \|H - \tilde{H}\| + O(\|H - \tilde{H}\|^2 \tau^2), \quad (20)$$

where $\|H - \tilde{H}\| << 1$ is assumed. The second term $\|e^{i\tilde{H}\tau} - \tilde{S}_{2k}^r\|$ in the epansion in Equation (19) is the Suzuki-Trotter error $\varepsilon_{Trotter}$. The Suzuki-Trotter error $\varepsilon_{Trotter}$ is approximated and upper-bounded by $$\left\|e^{i\tilde{H}\tau} - \tilde{S}_{2k}^r\right\| \approx r\left\|e^{i\tilde{H}\tau/r} - \tilde{S}_{2k}\right\| \leq \quad (21)$$

$$C_{2k} \frac{\tau^{2k+1}}{r^{2k}} \sum_{\gamma_1, \gamma_2, \ldots \gamma_{2k+1} \in \{\tilde{T}, \tilde{V}\}} [\gamma_1, [\gamma_2, \ldots [\gamma_{2k}, \gamma_{2k+1}]]],$$

where $C_{2k}$ is a constant value dependent on the order 2 k of the Suzuki-Trotter approximation. In the quantum Ewald sum, there is a third error sourse $$\left\|e^{i\tilde{H}_{Ewald}\tau} - \tilde{S}_{2k,Ewald}^r\right\|$$

due to the approximation used in the Ewald summation method and referred to as an Ewald sum error $\varepsilon_{Ewald}$. Thus, the total error in the quantum Ewald sum of the pair-wise Coulomb potential terms $\exp(iV_{jk}t)$ is then upper-bounded by $$\varepsilon_{QDE} = \|e^{iH\tau} - \tilde{S}_{2k,Ewald}^r\| \leq \quad (22)$$

$$\left\|e^{iH\tau} - e^{iH_{Ewald}\tau}\right\| + \left\|e^{iH_{Ewald}\tau} - e^{i\tilde{H}_{Ewald}\tau}\right\| + \left\|e^{i\tilde{H}_{Ewald}\tau} - \tilde{S}_{2k,Ewald}^r\right\|,$$

where $\tilde{S}_{2k,Ewald}^r$ denotes the evolution operator $S_{2k}$ shown in Equation (6) with the kinetic term T and the Coulomb potential energy V replaced by the finite-precision kinetic term $\tilde{T}$ and a finite-precision Coulomb potential term approximated in the Ewald summation method, $\tilde{V}_{Ewald}$, respectively.

IV.A Complexity Analysis for Direct Sum of Coulomb Potential Terms

In the 2 k-th order Suzuki-Trotter approximation, the evolution operator $U(\tau)$ is approximated as r repetitions of an evolution operator $S_{2k}$ for a time step $\delta t = \tau/r$. The Suzuki-Trotter error $\varepsilon_{Trotter}^{2k}$ in a single time step $\delta t$ of 2 k-th order Suzuki-Trotter approximation is $$\varepsilon_{Trotter}^{2k} = O(C_{2k}\eta^{2k+1}(\delta t)^{2k+1}), \quad (23)$$

where the constant value $C_{2k}$ is upper-bounded by $$C_{2k} \le |V_{max}|^{2k-1} c_2, \quad (24)$$

where $c_2$ is the operator norm of a two-particle commutator $\|[T_i, V_{ij}]\| \le 2T_{max}V_{max}$ with i and j denoting the two different particles, and $T_{max}$ and $V_{max}$ are the maximum operator norm $\|T_i\|$ and $\|V_{ij}\|$, respectively. In the following, it is discussed that both $T_{max}$ and $V_{max}$ are parameters that are scale free, i.e., the quantities have no η dependence.

As discussed above, an infinitely large system is to be simulated by simulating a unit cell of size $L^3$ containing η particles, repeated infinitely many times in all three spatial directions. This system can be scaled up while fixing all intensive variables until the simulation of a sufficiently scaled-up system emulates the target, infinitely large system well. Further scaling up the system from this point on, by the definition of convergence, must result in little difference in the quality of emulation. Since a successful simulation of an infinitely large system hinges on the existence of this convergence in any case, it may be assumed for all successful simulations with periodic boundary conditions, from the start, will have this convergence property.

For a simulation of a size that is sufficiently large to have reached the convergence, the kinetic energy operator of a constituent particle in a unit cell is considered as an example. It should be noted the following description has little to do with the quantum aspect of the simulation; a classical MD simulation is subject to essentially the same constraint. For example, a particle i has a large kinetic energy $T_i$ that exceeds $T_{FP}$, a finite-precision limited value of T. The error incurred for the i-th particle in the unit cell is denoted as $\varepsilon(T_{FP}, T_i)$. It should also be noted the cell is repeated infinitely many times, as per periodic boundary condition. For a v-cell subsystem of volume $vL^3$, the total error incurred then is $v\varepsilon(T_{FP}, T_i)$.

Further, an even larger unit cell of volume $(2L)^3$ is considered. Since the unit cell has eight times the volume, there are now eight times the number of particles that would have the finite-precision error in the kinetic energy operator compared to the previous case with the unit-cell volume of $L^3$. Once again, due to periodic boundary condition, the unit cell is repeated infinitely many times. As before, a subsystem, this time of volume $(v/8)(2L)^3$, can be considered so that the total volume of the subsystem of the target, infinitely large system to be simulated is kept the same. This subsystem also incurs a total error of $v\varepsilon(T_{FP}, T_i)$.

The agreement that has been observed is consistent with the fact that if two simulations have little difference due to the convergence, the errors incurred in the simulation of the target, infinitely large system must behave the same. In fact, such a behavior is necessary, if a periodic boundary condition based approach were to work as a method to simulate an infinitely large system. Thus, for simulating an infinite system, the operator norms, such as $\|T_i\|$, can be independent of η, and its maximal value $T_{max}$ can be set to be a constant. The choice of the maximum value indeed needs to be sufficiently large so that the simulation is sufficiently accurate in the first place. The amount of error incurred is expected to be the same for various η values. A similar argument applies for $V_{max}$. It should be noted that such a scaling argument cannot be made of systems that do not have periodic boundary condition.

Dependence on the time step δt in Equation (23) is directly due to the approximation of the evolution operator U(τ) as repetitions of an evolution operator $S_{2k}$ in the 2 k-th order Suzuki-Trotter approximation. The remaining dependence on the time step δt in Equation (23) is due to the fact that (i) the kinetic terms $T_i$ for i-th particles (i=0, 1, 2, ..., η−1) commute with one another, (ii) the Coulomb potential energies $V_{jk}$ for j-th and k-th particles (j, k=0, 1, 2, ..., η−1) commute with one another, and (iii) the kinetic terms $T_i$ and the Coulomb potential energies $V_{jk}$ do not commute with each other only if one of the particles to which the Couloumb potential energies $V_{jk}$ is applied is the particle to which the kinetic terms $T_i$ is applied to (i.e., i=j, or k). It should be noted the commutator bound expression for the Suzuki-Trotter error $a \in \varepsilon_{Trotter}^{2k}$ in a single time step δt in Equation (23) is a sum of nested commutators, each with 2 k+1 nesting stages (see also Equation (21)). At each nesting stage, there is either a kinetic term or Couloumb potential term V, with at least one appearance of T or V in total. Of all the nested commutators, the worst-scaling commutator with respect to the number of particles η is the commutator with a single kinetic term T and 2 k Coulomb potential terms V. For example, among the commutators between a kinetic term $T_i$ and all pair-wise Coulomb potential energies $V_{jk}$, the only non-zero commutators are with pair-wise Coulomb potential energies $V_{ij}$, where j≠i. For an additional nesting by a kinetic term $T_{j'}$, there are two cases: $T_i$ and $T_{j'}$, j'≠i. In the first case, all the matrix elements $V_{ij}$ do not commute. In the second case, only the matrix element $V_{ij}$ does not commute. Generalizing this to a further nesting by more kinetic terms, there are O(η) pair-wise Coulomb potential terms that do not commute if all kinetic terms are the same and there are O(1) pair-wise potential terms that do not commute if all kinetic terms are chosen to act on two specific particles only. In an additional nesting by pair-wise Coulomb potential terms to a commutator between $T_i$ and $V_{ij}$, all $V_{ij}$ with j≠i in the additional pair-wise Coulomb potential terms used in the nesting do not commute. Thus, the scaling of the nested commutator with respect to the number of particles η may be written as $O(\eta^{2k'+1})$, where k' is the number of pair-wise Coulomb potential terms that appear in the nested commutator expression in Equation (21). In Equation (23), the worst scaling term in η, i.e., k'=k, is considered.

In the direct sum, the total Suzuki-Trotter error $\varepsilon_{Trotter}$ then is $$\varepsilon_{Trotter} = r \times \epsilon_{Trotter}^{2k} = O\left(C_{2k}\frac{\tau}{\delta t}\eta^{2k+1}(\delta t)^{2k+1}\right) = O(\tau\eta^{2k+1}(\delta t)^{2k}). \quad (25)$$

As discussed above, a total error $\varepsilon_{DCS}$ in the direct sum of the Coulomb potential terms includes the Suzuki-Trotter errors $\varepsilon_{Trotter}$ and the finite-precision error $\varepsilon_{FP}$. Since there are more pair-wise Coulomb potential terms $V_{jk}$ than the kinetic terms $T_i$, the computational complexity is mainly determined by the summation of the pair-wise Coulomb potential terms $V_{jk}$, as $O(\eta^2)$. Each of the pair-wise Coulomb potential terms $V_{jk}$ can be implemented by application of a combination of gate operations to the position registers for j-th and k-th particles, by a system controller, such as the system controller 104. In some embodiments, the combination of gate operations include single-qubit gate operations and two-qubit gate operations. The accuracy of the implementation of the the pair-wise Coulomb potential terms $V_{jk}$ depends on the the edge length Δ of the discritized grids of the unit cell, and assumed to be of the same order as $O(\Delta)$. The total finite-precision error $\varepsilon_{FP}$ for the simulation is then given by $$\varepsilon_{FP}=\tau\|H-\tilde{H}\|=O(\tau\|V-\tilde{V}\|)=O(\tau\eta^2\Delta). \quad (26)$$

The total error $\varepsilon_{DCS}$ in the direct sum of the Coulomb potential terms is therefore $$\varepsilon_{DCS}=\varepsilon_{FP}+\varepsilon_{Trotter}=O(\tau\eta^2\Delta)+O(\tau\eta^{2k+1}(\delta t)^{2k}). \quad (27)$$

To suppress the total error $\varepsilon_{DCS}$ to a constant value, the first term is suppressed by requiring $$\Delta^{-1}=O(\tau\eta^2), \quad (28)$$

and the second term is suppressed to a constant value, by requiring $$(\delta t)^{-1}=O((\tau\eta^{2k+1})^{1/2k})=O(\eta^{1+1/(2k)}\tau^{1/(2k)}). \quad (29)$$

Using these scalings, the number of evaluations of the pair-wise Coulomb potential terms is $$\#_{queries}=O(r\eta^2)=O\left(\frac{\tau}{\delta r}\eta^2\right)=O(\eta^{3+1/(2k)}\tau^{1+1/(2k)}). \quad (30)$$

As discussed in Subsection III.A, the time duration $\tau$ of the evolution operator $U(\tau)$ to be simulated scales as $O(\eta^{2/3})$. Thus, the number of queries to the pair-wise Coulomb potential terms scales with respect to the number of particles $\eta$ as $$\#_{queries}=O(\eta^{11/3+5/(6k)})). \quad (31)$$

Each pair-wise Coulomb potential term $V_{jk}$ can be implemented by application of a combination of gate operations toposition register of size $\mathcal{O}(\log_2 N)$ with $N \propto \Delta^{-3}$. The combination of gate operations can be performed with circuits of size $O(\text{poly}(\log N))$. Therefore, the gate complexity is given by $$\#_{gates}=O((\eta^{11/3+5/(6k)})\text{polylog}(\eta)). \quad (32)$$

It should be noted that the time duration $\tau \propto \eta^{2/3}$ and $N \propto L^3\Delta^{-3}=O(\tau^{3/2}(\tau\eta^2)^3)$, the best-known gate complexity by conventional method is of $\tilde{O}(\tau\eta^{8/3}N^{1/3})=\tilde{O}(\eta^{6+1/3})$. Thus, the method of computing the direct sum of the Coulomb potential terms in molecular dynamics (MD) simulations according to the embodiments described herein provides an improvement in gate complexity over the conventional methods.

IV. Complexity Analysis for Quantum Ewald Sum of Coulomb Potential Terms

The main benefit of the quantum Ewald sum over the direct sum is reduction in the number of the Couloumb potential terms. It is assumed that the Ewald sum error $\varepsilon_{Ewald}$ the first term in Equation (22)) is proportional to the time duration $\tau$ of the evolution operator $U(\tau)$ to be simulated, $\varepsilon_{Ewald} \approx \tau\varepsilon_{Ewald}$. The number of terms in the sum of the short-range interaction $V_{short}$ is $O(\eta^{3/2}(\log(1/\varepsilon_{Ewald}))^{3/2})$ and the number of terms in the sum of the long-range interaction $V_{long}$ is $O(\eta^{1/2}(\log(1/\varepsilon_{Ewald}))^{3/2})]$.

To compute the Suzuki-Trotter error $\varepsilon_{Trotter}$ in the quantum Ewald sum, it should be noted that the direct sum is merely approximated as $$\|V_{Ewald}-V_{Coulomb}\|=O(\varepsilon_{Ewald}). \quad (33)$$

Thus, $$\varepsilon_{Trotter}=O(\tau\eta^{2k+1}(\delta t)^{2k})+O(\varepsilon_{Ewald}) \quad (34)$$

To now calculate the finite-precision error $\varepsilon_{FP}$, the number of terms in the sum of the short-range interaction (because the sum of the long-range interaction has fewer terms) is considered. There are $O(\eta^{3/2}(\log(1/\varepsilon_{Ewald}))^{3/2})$ terms in the sum of the short-range interaction. The finite-precision error $\varepsilon_{FP}$ is then $$\varepsilon_{FP}=\tau\|H_{Ewald}-\tilde{H}_{Ewald}\|= \quad (35)$$
$$O(\tau\|V_{Ewald}-\tilde{V}_{Ewald}\|)=O(\Delta\tau\eta^{3/2}(\log(1/\varepsilon_{Ewald}))^{3/2}).$$

The total error $\varepsilon_{QDE}$ for the quantum Ewald sum of the pair-wise Coulomb potential terms $\exp(iV_{jk}t)$ for j-th and k-th particles (j, k=0, 1, 2, . . . , $\eta-1$) is therefore, $$\varepsilon_{QDE} \approx \varepsilon_{Ewald}+\varepsilon_{FP}+\varepsilon_{Trotter} \quad (36)$$
$$=O(\tau\varepsilon_{Ewald})+O(\Delta\tau\eta^{3/2}(\log(1/\varepsilon_{Ewald}))^{3/2})+O(\tau\eta^{2k+1}(\delta t)^{2k}) \quad (37)$$

The first and second term in Equation (37) are suppressed by requiring $$\varepsilon_{Ewald}=O(1/\tau), -^{-1}=O(\tau\eta^{3/2}(\log \tau)^{3/2})), \quad (38)$$

and the third term is suppressed by requiring $$(\delta t)^{-1}=O(\eta^{1+1/(2k)}\tau^{1/(2k)}). \quad (39)$$

The number of queries for the sum of the short-range interaction and the sum of long-range interaction, discussed below, is given by $$\#_{queries,short}=\tau\eta^{3/2}(\log(1/\varepsilon_{Ewald}))^{3/2}= O(\tau^{1+1/(2k)}\eta^{5/2+1/(2k)}\log^3(\tau)) \quad (40)$$

and $$\#_{queries,short}=\tau\eta^{1/2}(\log(1/\varepsilon_{Ewald}))^{3/2}= O(\tau^{1+1/(2k)}\eta^{3/2+1/(2k)}\log^3(\tau)) \quad (41)$$

The type of queries differs for the sum of the short-range interaction and the long-range interactions. Queries for the sum of the short-range interactions act on a pair of particles. Queries for the sum of the long-range interactions act on all particles (see Equation (13)). It is assumed that a query for the sum of the short-range interactions has gate complexity of $\tilde{O}(1)$ and a query for the sum of the long-range interactions has gate complexity of $\tilde{O}(\eta)$. Since the time duration $\tau$ of the evolution operator $U(\tau)$ to be simulated scales as $O(\eta^{2/3})$, an overall gate complexity is $$\#_{gates}=\tilde{O}(\eta^{19/6+5/(6k)}), \quad (42)$$

which is better than the complexity for the direct sum of the pair-wise Coulomb potential terms $\exp(iV_{jk}t)$ for j-th and k-th particles (j, k=0, 1, 2, . . . , $\eta-1$) in Equation (32). Thus, the method of computing the quantum Ewald sum of the Coulomb potential terms in molecular dynamics (MD) simulations according to the embodiments described herein provides an improvement in gate complexity over the conventional methods.

FIG. 7 depicts a flowchart illustrating a method 700 used to perform a computational process using a quantum computer.

In block 710, by a system controller, a first register of a quantum processor is transformed to a charge encoded state in which charges of a plurality of interacting particles to be simulated are encoded.

In block 720, by the system controller, a second register of the quantum processor is transformed to a position encoded state in which positions of the plurality of interacting particles are encoded.

In block 730, a first phase shift operation is performed. The first phase shift operation includes shifting, by the system controller, a phase of the first and second registers by kinetic energies of the plurality of interacting particles.

In block 740, a second phase shift operation is performed. The second phase shift operation includes shifting, by the system controller, the phase of the first and second registers by pair-wise Coulomb potential energies of the plurality of interacting particles.

In block 750, by the system controller, the phase of the first and second registers is measured.

In block 760, by the system controller, the measured phase of the first and second registers is transmitted to a classical computer. The measured phase includes a sum of the kinetic energies and the pair-wise Coulomb potential energies of the plurality of interacting particles;

In block 770, by the classical computer, results of simulation of the plurality of interacting particles that are based on the measured phase transmitted from the system controller are outputted. The results of the simulation are configured to be displayed on a user interface, stored in a memory of the classical computer, or transferred to another computational device.

The method of obtaining energies of a system having interacting particles by molecular dynamics (MD) simulations described herein provides a complexity improvement by use of a quantum processor in the calculation of Ewald summation method over the classical calculation method.

While the foregoing is directed to specific embodiments, other and further embodiments may be devised without departing from the basic scope thereof, and the scope thereof is determined by the claims that follow.

The invention claimed is:

1. A method of performing a computational process to simulate a plurality of interacting particles using a quantum computing system comprising a classical computer and a quantum processor, the method comprising:
   applying, by a system controller, a combination of single-qubit gate operations and two-qubit-gate operations to a first register of a plurality of qubits of the quantum processor, to transform the first register to a charge encoded state in which charges of the plurality of interacting particles to be simulated are encoded;
   applying, by the system controller, a combination of single-qubit gate operations and two-qubit-gate operations to a second register of a plurality of qubits of the quantum processor, to transform the second register to a position encoded state in which positions of the plurality of interacting particles are encoded;
   performing a first phase shift operation, comprising shifting, by the system controller, a phase of the first and second registers by kinetic energies of the plurality of interacting particles;
   performing a second phase shift operation, comprising shifting, by the system controller, the phase of the first and second registers by pair-wise Coulomb potential energies of the plurality of interacting particles;
   measuring, by the system controller, the phase of the first and second registers; and
   transmitting, by the system controller, the measured phase of the first and second registers to the classical computer, the measured phase comprising a sum of the kinetic energies and the pair-wise Coulomb potential energies of the plurality of interacting particles.

2. The method according to claim 1, wherein the applying, of the combination of single-qubit gate operations and two-qubit-gate operations to the first register comprises controlling, by the system controller, one or more lasers configured to emit laser beams, which are provided to the quantum processor.

3. The method according to claim 1, wherein the applying of the combination of single-qubit gate operations and two-qubit-gate operations to the second register comprises controlling, by the system controller, one or more lasers configured to emit laser beams, which are provided to the quantum processor.

4. The method according to claim 1, wherein the first phase shift operation comprises:
   a quantum discrete Fourier transformation by applying, by the system controller, a combination of single-qubit gate operations and two-qubit-gate operations to the second register; and
   a phase-kickback transformation by applying, by the system controller, a combination of single-qubit gate operations and two-qubit-gate operations to the second register.

5. The method according to claim 1, wherein
   the second phase shift operation comprises:
      shifting the phase of the first and second registers by short-range interactions of the plurality of interacting particles;
      shifting the phase of the first and second registers by long-range interactions of the plurality of interacting particles; and
      shifting the phase of the first and second registers by self-energies of the plurality of interacting particles, and
   the pair-wise Coulomb potential energies of the plurality of interacting particles comprise the short-range interactions, the long-range interactions, and the self-energies of the plurality of interacting particles.

6. The method according to claim 5, wherein
   the shifting of the phase of the first and second registers by short-range interactions of the plurality of interacting particles comprises a phase-kickback transformation by applying, by the system controller, a combination of single-qubit gate operations and two-qubit-gate operations to the second register,
   the shifting of the phase of the first and second registers by long-range interactions of the plurality of interacting particles comprises a phase-kickback transformation by applying, by the system controller, a combination of single-qubit gate operations and two-qubit-gate operations to the second register, and
   the shifting of the phase of the first and second registers by self-energies of the plurality of interacting particles comprises a phase-kickback transformation by applying, by the system controller, a combination of single-qubit gate operations and two-qubit-gate operations to the second register.

7. The method according to claim 1, wherein the quantum processor comprises a group of trapped ions, each of which has two frequency-separated states defining a qubit.

8. A quantum computing system, comprising:
   a quantum processor comprising a group of trapped ions, each trapped ion of the group of trapped ions having two hyperfine states defining a qubit; and a system controller configured to:
  apply a combination of single-qubit gate operations and two-qubit-gate operations to a first register of a plurality of qubits of the quantum processor, to transform the first register to a charge encoded state in which charges of a plurality of interacting particles to be simulated are encoded;
  apply a combination of single-qubit gate operations and two-qubit-gate operations to a second register of a plurality of qubits of the quantum processor, to transform the second register to a position encoded state in which positions of the plurality of interacting particles are encoded;
  perform a first phase shift operation, comprising shifting a phase of the first and second registers by kinetic energies of the plurality of interacting particles;
  perform a second phase shift operation, comprising shifting the phase of the first and second registers by pair-wise Coulomb potential energies of the plurality of interacting particles;
  measure, by the system controller, the phase of the first and second registers; and
  transmit the measured phase of the first and second registers to a classical computer, the measured phase comprising a sum of the kinetic energies and the pair-wise Coulomb potential energies of the plurality of interacting particles.

9. The quantum computing system according to claim 8, wherein the applying of the combination of single-qubit gate operations and two-qubit-gate operations to the first register comprises controlling, by the system controller, one or more lasers configured to emit laser beams, which are provided to the quantum processor.

10. The quantum computing system according to claim 8, wherein the applying of the combination of single-qubit gate operations and two-qubit-gate operations to the second register comprises controlling, by the system controller, one or more lasers configured to emit laser beams, which are provided to the quantum processor.

11. The quantum computing system according to claim 8, wherein the first phase shift operation comprises:
  a quantum discrete Fourier transformation by applying, by the system controller, a combination of single-qubit gate operations and two-qubit-gate operations to the second register; and
  a phase-kickback transformation by applying, by the system controller, a combination of single-qubit gate operations and two-qubit-gate operations to the second register.

12. The quantum computing system according to claim 8, wherein
  the second phase shift operation comprises:
    shifting the phase of the first and second registers by short-range interactions of the plurality of interacting particles;
    shifting the phase of the first and second registers by long-range interactions of the plurality of interacting particles; and
    shifting the phase of the first and second registers by self-energies of the plurality of interacting particles, and
  the pair-wise Coulomb potential energies of the plurality of interacting particles comprise the short-range interactions, the long-range interactions, and the self-energies of the plurality of interacting particles.

13. The quantum computing system according to claim 12, wherein
  the shifting of the phase of the first and second registers by short-range interactions of the plurality of interacting particles comprises a phase-kickback transformation by applying, by the system controller, a combination of single-qubit gate operations and two-qubit-gate operations to the second register,
  the shifting of the phase of the first and second registers by long-range interactions of the plurality of interacting particles comprises a phase-kickback transformation by applying, by the system controller, a combination of single-qubit gate operations and two-qubit-gate operations to the second register, and
  the shifting of the phase of the first and second registers by self-energies of the plurality of interacting particles comprises a phase-kickback transformation by applying, by the system controller, a combination of single-qubit gate operations and two-qubit-gate operations to the second register.

14. A quantum computing system comprising a quantum processor and a classical computer having non-volatile memory having a number of instructions stored therein which, when executed by one or more processors, causes the quantum computing system to perform operations comprising:
  applying, by a system controller, a combination of single-qubit gate operations and two-qubit-gate operations to a first register of a plurality of qubits of the quantum processor, to transform the first register to a charge encoded state in which charges of a plurality of interacting particles to be simulated are encoded;
  applying, by the system controller, a combination of single-qubit gate operations and two-qubit-gate operations to a second register of a plurality of qubits of the quantum processor, to transform the second register to a position encoded state in which positions of the plurality of interacting particles are encoded;
  performing a first phase shift operation, comprising shifting, by the system controller, a phase of the first and second registers by kinetic energies of the plurality of interacting particles;
  performing a second phase shift operation, comprising shifting, by the system controller, the phase of the first and second registers by pair-wise Coulomb potential energies of the plurality of interacting particles;
  measuring, by the system controller, the phase of the first and second registers; and
  transmitting, by the system controller, the measured phase of the first and second registers to the classical computer, the measured phase comprising a sum of the kinetic energies and the pair-wise Coulomb potential energies of the plurality of interacting particles.

15. The quantum computing system according to claim 14, wherein the applying of the combination of single-qubit gate operations and two-qubit-gate operations to the first register.

16. The quantum computing system according to claim 14, wherein the applying of the combination of single-qubit gate operations and two-qubit-gate operations to the second register.

17. The quantum computing system according to claim 14, wherein the first phase shift operation comprises:
- a quantum discrete Fourier transformation by applying, by the system controller, a combination of single-qubit gate operations and two-qubit-gate operations to the second register; and
- a phase-kickback transformation by applying, by the system controller, a combination of single-qubit gate operations and two-qubit-gate operations to the second register.

18. The quantum computing system according to claim 14, wherein
the second phase shift operation comprises:
- shifting the phase of the first and second registers by short-range interactions of the plurality of interacting particles;
- shifting the phase of the first and second registers by long-range interactions of the plurality of interacting particles; and
- shifting the phase of the first and second registers by self-energies of the plurality of interacting particles, and the pair-wise Coulomb potential energies of the plurality of interacting particles comprise the short-range interactions, the long-range interactions, and the self-energies of the plurality of interacting particles.

19. The quantum computing system according to claim 18, wherein
the shifting of the phase of the first and second registers by short-range interactions of the plurality of interacting particles comprises a phase-kickback transformation by applying, by the system controller, a combination of single-qubit gate operations and two-qubit-gate operations to the second register, the shifting of the phase of the first and second registers by long-range interactions of the plurality of interacting particles comprises a phase-kickback transformation by applying, by the system controller, a combination of single-qubit gate operations and two-qubit-gate operations to the second register, and the shifting of the phase of the first and second registers by self-energies of the plurality of interacting particles comprises a phase-kickback transformation by applying, by the system controller, a combination of single-qubit gate operations and two-qubit-gate operations to the second register.

20. The quantum computing system according to claim 14, wherein the quantum processor comprises a group of trapped ions, each of which has two frequency-separated states defining a qubit.

* * * * *